United States Patent
Lowe et al.

(10) Patent No.: US 11,547,625 B2
(45) Date of Patent: *Jan. 10, 2023

(54) REINFORCED THERAPEUTIC WRAP AND METHOD

(71) Applicant: Avent, Inc., Alpharetta, GA (US)

(72) Inventors: Mark H. Lowe, Danville, CA (US); Krister Bowman, Oakland, CA (US)

(73) Assignee: AVENT, INC., Alpharetta, GA (US)

( * ) Notice: Subject to any disclaimer, the term of this patent is extended or adjusted under 35 U.S.C. 154(b) by 787 days.

This patent is subject to a terminal disclaimer.

(21) Appl. No.: 15/483,980

(22) Filed: Apr. 10, 2017

(65) Prior Publication Data

US 2017/0216129 A1    Aug. 3, 2017

Related U.S. Application Data

(63) Continuation of application No. 14/095,954, filed on Dec. 3, 2013, now Pat. No. 9,615,967, which is a (Continued)

(51) Int. Cl.
*A61H 9/00* (2006.01)
*A61F 7/02* (2006.01)
(Continued)

(52) U.S. Cl.
CPC .............. *A61H 9/0078* (2013.01); *A61F 7/02* (2013.01); *A61H 9/0092* (2013.01);
(Continued)

(58) Field of Classification Search
CPC .... A61H 9/005; A61H 9/0078; A61H 9/0092; A61H 2201/0103; A61H 2201/0107;
(Continued)

(56) References Cited

U.S. PATENT DOCUMENTS 1,886,768 A    11/1932    Watson
1,958,899 A    5/1934    MacAdams
(Continued)

FOREIGN PATENT DOCUMENTS

CN    2304378 Y    1/1999
CN    1373649 A    10/2002
(Continued)

OTHER PUBLICATIONS

Gallagher Corp. Polyurethane Hardness. Gallagher. https://gallaghercorp.com/polyurethane-durometer-hardness/. Updated 2020. Accessed Apr. 9, 2020 (Year: 2020).*
(Continued)

*Primary Examiner* — Camtu T Nguyen
(74) *Attorney, Agent, or Firm* — Meunier Carlin & Curfman LLC

(57) ABSTRACT

A therapy wrap for treatment of at least a portion of an animate body having improved kink resistance. The therapy wrap may be selectively reinforced for improved kink resistance in only a portion of the wrap. The reinforcement may decrease the kink radius. The wrap may include a kink reducer in all or only a selected kink-prone region. The kink reducer may be selectively configured attachment points or spot welds. The therapy wrap may include a reinforcement layer of one or more discrete reinforcement members. The wrap may be formed by pre-tensioning the material layers while forming the fluid bladder and/or gas pressure bladder. The therapy wrap may be adapted to compensate for conditions that normally cause kinking of the wrap or buckling of the fluidic channels. Also disclosed are methods of manufacturing the wrap and methods of administering a temperature-controlled treatment to an anatomical body part.

20 Claims, 18 Drawing Sheets

Related U.S. Application Data continuation-in-part of application No. 12/982,266, filed on Dec. 30, 2010, now Pat. No. 8,597,217.

(51) Int. Cl.

| | |
|---|---|
| *A61F 7/00* | (2006.01) |
| *B29L 22/02* | (2006.01) |
| *B29C 65/00* | (2006.01) |
| *B29C 65/02* | (2006.01) |
| *B29C 65/04* | (2006.01) |

(52) U.S. Cl.
CPC . *A61F 2007/003* (2013.01); *A61F 2007/0032* (2013.01); *A61F 2007/0042* (2013.01); *A61F 2007/0054* (2013.01); *A61F 2007/0091* (2013.01); *A61F 2007/0274* (2013.01); *A61H 2201/0103* (2013.01); *A61H 2201/0107* (2013.01); *A61H 2201/0207* (2013.01); *A61H 2201/0214* (2013.01); *A61H 2201/0242* (2013.01); *A61H 2201/165* (2013.01); *A61H 2201/169* (2013.01); *B29C 65/02* (2013.01); *B29C 65/04* (2013.01); *B29C 66/21* (2013.01); *B29C 66/221* (2013.01); *B29C 66/439* (2013.01); *B29C 66/71* (2013.01); *B29C 66/723* (2013.01); *B29C 66/7292* (2013.01); *B29L 2022/025* (2013.01)

(58) Field of Classification Search
CPC ........ A61H 2201/165; A61H 2201/169; A61H 2201/1697; A61F 13/06; A61F 13/016; A61F 13/08; A61F 5/012; A61F 5/05816; A61F 5/05833
See application file for complete search history.

(56) References Cited

U.S. PATENT DOCUMENTS

| | | | |
|---|---|---|---|
| 2,146,622 A | 2/1939 | Carlo | |
| 2,148,661 A | 2/1939 | Thierer | |
| 2,413,386 A | 12/1946 | Schulz | |
| 2,510,125 A | 6/1950 | Meakin | |
| 2,531,074 A | 11/1950 | Miller | |
| 2,540,547 A | 2/1951 | Rodert | |
| 2,608,690 A | 9/1952 | Kolb et al. | |
| 2,703,770 A | 3/1955 | Melzer | |
| 2,726,658 A | 12/1955 | Chessey | |
| 2,954,898 A | 10/1960 | Feeberg | |
| 3,261,042 A | 7/1966 | Baker | |
| 3,320,682 A | 5/1967 | Sliman | |
| 3,354,898 A | 11/1967 | Barnes | |
| 3,559,640 A | 2/1971 | Beckett | |
| 3,561,435 A | 2/1971 | Nicholson | |
| 3,738,367 A | 6/1973 | Hardy | |
| 3,744,555 A | 7/1973 | Fletcher et al. | |
| 3,830,676 A | 8/1974 | Elkins | |
| 3,871,381 A | 3/1975 | Roslonski | |
| 3,901,225 A | 8/1975 | Sconce | |
| 3,993,053 A | 11/1976 | Grossan | |
| 4,020,209 A | 4/1977 | Yuan | |
| 4,026,299 A | 5/1977 | Sauder | |
| 4,116,476 A | 9/1978 | Porter et al. | |
| 4,118,946 A | 10/1978 | Tubin | |
| 4,147,921 A | 4/1979 | Waller et al. | |
| 4,149,529 A | 4/1979 | Copeland et al. | |
| 4,149,541 A | 4/1979 | Gammons et al. | |
| 4,170,998 A | 10/1979 | Sauder | |
| 4,184,537 A | 1/1980 | Sauder | |
| 4,194,247 A | 3/1980 | Melander | |
| 4,320,746 A | 3/1982 | Arkans et al. | |
| 4,335,726 A | 6/1982 | Kolsledt | |
| 4,338,944 A | 7/1982 | Arkans | |
| D269,379 S | 6/1983 | Bledsoe | |
| 4,407,276 A | 10/1983 | Bledsoe | |
| 4,412,648 A | 11/1983 | Ford et al. | |
| 4,436,125 A | 3/1984 | Blenkush | |
| 4,441,504 A | 4/1984 | Peterson et al. | |
| 4,460,085 A | 7/1984 | Jantzen | |
| 4,463,751 A | 8/1984 | Bledsoe | |
| 4,471,759 A | 9/1984 | Anderson et al. | |
| 4,478,436 A | 10/1984 | Hashimoto | |
| 4,547,906 A | 10/1985 | Nishida | |
| 4,550,828 A | 11/1985 | Baldwin et al. | |
| 4,597,384 A | 7/1986 | Whitney | |
| 4,678,027 A | 7/1987 | Shirey et al. | |
| 4,691,762 A | 9/1987 | Elkins et al. | |
| 4,699,613 A | 10/1987 | Donawick et al. | |
| 4,718,429 A | 1/1988 | Smidt | |
| 4,738,119 A | 4/1988 | Zafred | |
| 4,753,268 A | 6/1988 | Palau | |
| 4,765,338 A | 8/1988 | Turner et al. | |
| 4,817,588 A | 4/1989 | Bledsoe | |
| 4,834,073 A | 5/1989 | Bledsoe et al. | |
| 4,844,072 A | 7/1989 | French et al. | |
| 4,884,304 A | 12/1989 | Elkins | |
| 4,925,603 A | 5/1990 | Nambu | |
| 4,955,369 A | 9/1990 | Bledsoe | |
| 4,955,435 A | 9/1990 | Shuster et al. | |
| 4,962,761 A | 10/1990 | Golden | |
| 4,964,282 A | 10/1990 | Wagner | |
| 4,964,402 A | 10/1990 | Grim et al. | |
| 4,966,145 A | 10/1990 | Kikumoto et al. | |
| 4,976,262 A | 12/1990 | Palmacci | |
| 5,002,270 A | 3/1991 | Shine | |
| 5,014,695 A | 5/1991 | Benak et al. | |
| 5,022,109 A | 6/1991 | Pekar | |
| 5,033,136 A | 7/1991 | Elkins | |
| 5,052,725 A | 10/1991 | Meyer et al. | |
| 5,056,563 A | 10/1991 | Glossop | |
| 5,072,875 A | 12/1991 | Zacoi | |
| 5,074,285 A | 12/1991 | Wright | |
| 5,076,068 A | 12/1991 | Mikhail | |
| 5,080,089 A | 1/1992 | Mason et al. | |
| 5,080,166 A | 1/1992 | Haugeneder | |
| 5,086,771 A | 2/1992 | Molloy | |
| 5,097,829 A | 3/1992 | Quisenberry | |
| 5,104,158 A | 4/1992 | Meyer et al. | |
| 5,112,045 A | 5/1992 | Mason et al. | |
| 5,113,877 A | 5/1992 | Johnson, Jr. et al. | |
| 5,163,425 A | 11/1992 | Nambu et al. | |
| 5,163,923 A | 11/1992 | Donawick et al. | |
| 5,172,689 A | 12/1992 | Wright | |
| 5,186,698 A | 2/1993 | Mason et al. | |
| 5,201,552 A | 4/1993 | Hohmann et al. | |
| 5,230,335 A | 7/1993 | Johnson, Jr. et al. | |
| 5,232,020 A | 8/1993 | Mason et al. | |
| 5,241,951 A | 9/1993 | Mason et al. | |
| 5,243,706 A | 9/1993 | Frim et al. | |
| 5,269,369 A | 12/1993 | Faghri | |
| D345,609 S | 3/1994 | Mason et al. | |
| 5,294,156 A | 3/1994 | Kumazaki et al. | |
| D345,802 S | 4/1994 | Mason et al. | |
| D345,803 S | 4/1994 | Mason et al. | |
| 5,303,716 A | 4/1994 | Mason et al. | |
| 5,305,712 A | 4/1994 | Goldstein | |
| 5,314,455 A | 5/1994 | Johnson, Jr. et al. | |
| 5,316,250 A | 5/1994 | Mason et al. | |
| 5,316,547 A | 5/1994 | Gildersleeve | |
| D348,106 S | 6/1994 | Mason et al. | |
| 5,324,319 A | 6/1994 | Mason et al. | |
| D348,518 S | 7/1994 | Mason et al. | |
| D351,472 S | 10/1994 | Mason et al. | |
| 5,352,174 A | 10/1994 | Mason et al. | |
| 5,353,605 A | 10/1994 | Naaman | |
| 5,354,101 A | 10/1994 | Anderson, Jr. | |
| 5,354,103 A | 10/1994 | Torrence et al. | |
| D352,781 S | 11/1994 | Mason et al. | |
| 5,372,575 A | 12/1994 | Sebastian | |
| 5,383,689 A | 1/1995 | Wolfe, Sr. | |
| 5,383,919 A | 1/1995 | Kelly et al. | |
| RE34,883 E | 3/1995 | Grim | |
| 5,395,399 A | 3/1995 | Rosenwald | |
| 5,407,421 A | 4/1995 | Goldsmith | |

(56) References Cited

U.S. PATENT DOCUMENTS

| | | |
|---|---|---|
| 5,411,541 A | 5/1995 | Bell et al. |
| 5,415,625 A | 5/1995 | Cassford et al. |
| 5,417,720 A | 5/1995 | Mason |
| 5,427,577 A | 6/1995 | Picchietti et al. |
| 5,441,533 A | 8/1995 | Johnson et al. |
| 5,449,379 A | 9/1995 | Hadtke |
| 5,451,201 A | 9/1995 | Prengler |
| 5,466,250 A | 11/1995 | Johnson, Jr. et al. |
| 5,468,220 A | 11/1995 | Sucher |
| 5,470,353 A | 11/1995 | Jensen |
| 5,476,489 A | 12/1995 | Koewler |
| 5,484,448 A | 1/1996 | Steele et al. |
| 5,494,074 A | 2/1996 | Ramacier, Jr. et al. |
| 5,496,358 A | 3/1996 | Rosenwaid |
| 5,507,792 A | 4/1996 | Mason et al. |
| 5,509,894 A | 4/1996 | Mason et al. |
| 5,514,081 A | 5/1996 | Mann |
| 5,520,622 A | 5/1996 | Bastyr et al. |
| 5,524,293 A | 6/1996 | Kung |
| 5,527,268 A | 6/1996 | Gildersleeve et al. |
| 5,533,354 A | 7/1996 | Pirkle |
| 5,539,934 A | 7/1996 | Ponder |
| D372,534 S | 8/1996 | Andrews et al. |
| 5,553,712 A | 9/1996 | Tisbo et al. |
| 5,554,119 A | 9/1996 | Harrison |
| 5,556,138 A | 9/1996 | Nakajima et al. |
| 5,564,124 A | 10/1996 | Elsherif et al. |
| 5,569,172 A | 10/1996 | Padden et al. |
| 5,592,694 A | 1/1997 | Yewer |
| 5,609,620 A | 3/1997 | Daily |
| 5,630,328 A | 5/1997 | Hise et al. |
| 5,634,940 A | 6/1997 | Panyard |
| 5,638,707 A | 6/1997 | Gould |
| 5,645,671 A | 7/1997 | Tillinghast |
| D382,113 S | 8/1997 | DuRapau |
| D383,547 S | 9/1997 | Mason et al. |
| D383,848 S | 9/1997 | Mason et al. |
| 5,662,239 A | 9/1997 | Heuvelman |
| 5,662,695 A | 9/1997 | Mason et al. |
| 5,672,152 A | 9/1997 | Mason et al. |
| 5,683,118 A | 11/1997 | Slocum |
| 5,716,388 A | 2/1998 | Petelle |
| 5,728,058 A | 3/1998 | Ouellette et al. |
| 5,732,464 A | 3/1998 | Lamont |
| 5,755,275 A | 5/1998 | Rose et al. |
| 5,755,755 A | 5/1998 | Panyard |
| 5,769,801 A | 6/1998 | Tumey et al. |
| 5,772,618 A | 6/1998 | Mason et al. |
| 5,782,780 A | 7/1998 | Mason et al. |
| 5,792,216 A | 8/1998 | Kappel |
| 5,807,294 A | 9/1998 | Cawley et al. |
| 5,827,208 A | 10/1998 | Mason et al. |
| 5,833,638 A | 11/1998 | Nelson |
| 5,862,675 A | 1/1999 | Scaringe et al. |
| 5,865,841 A | 2/1999 | Kolen et al. |
| 5,866,219 A | 2/1999 | McClure et al. |
| 5,868,690 A | 2/1999 | Eischen, Sr. |
| 5,871,526 A | 2/1999 | Gibbs et al. |
| 5,895,418 A | 4/1999 | Ringer |
| 5,913,885 A | 6/1999 | Klatz et al. |
| 5,920,934 A | 7/1999 | Hannagan et al. |
| 5,951,598 A | 9/1999 | Bishay et al. |
| 5,967,225 A | 10/1999 | Jenkins |
| 5,968,072 A | 10/1999 | Hite et al. |
| 5,970,519 A | 10/1999 | Weber |
| 5,980,561 A | 11/1999 | Kolen et al. |
| 5,984,885 A | 11/1999 | Gaylord, Jr. et al. |
| 5,989,285 A | 11/1999 | DeVilbiss et al. |
| 5,992,459 A | 11/1999 | Sugita et al. |
| 5,997,495 A | 12/1999 | Cook et al. |
| 6,030,412 A | 2/2000 | Klatz et al. |
| 6,036,107 A | 3/2000 | Aspen et al. |
| 6,036,718 A | 3/2000 | Ledford et al. |
| 6,048,326 A | 4/2000 | Davis et al. |
| 6,053,169 A | 4/2000 | Hunt |
| 6,055,670 A | 5/2000 | Parker |
| 6,058,508 A | 5/2000 | Brown Honeysuckle |
| 6,074,413 A | 6/2000 | Davis et al. |
| 6,083,256 A | 7/2000 | Der Ovanesian |
| 6,089,593 A | 7/2000 | Hanson et al. |
| D430,288 S | 8/2000 | Mason et al. |
| D430,289 S | 8/2000 | Mason et al. |
| 6,105,382 A | 8/2000 | Reason |
| 6,109,338 A | 8/2000 | Butzer |
| 6,117,164 A * | 9/2000 | Gildersleeve ............. A61F 7/02 607/108 |
| 6,146,347 A | 11/2000 | Porrata |
| 6,146,413 A | 11/2000 | Harman |
| 6,156,059 A | 12/2000 | Olofsson |
| 6,178,562 B1 | 1/2001 | Elkins |
| 6,228,106 B1 | 5/2001 | Simbruner et al. |
| 6,238,427 B1 | 5/2001 | Matta |
| 6,254,554 B1 | 7/2001 | Turtzo |
| 6,260,890 B1 | 7/2001 | Mason |
| 6,261,314 B1 | 7/2001 | Rich |
| 6,270,481 B1 | 8/2001 | Mason et al. |
| 6,306,112 B2 | 10/2001 | Bird |
| 6,328,276 B1 | 12/2001 | Falch et al. |
| 6,349,412 B1 | 2/2002 | Dean |
| 6,352,550 B1 | 3/2002 | Gildersleeve et al. |
| 6,354,635 B1 | 3/2002 | Dyson et al. |
| 6,361,514 B1 | 3/2002 | Brown et al. |
| 6,368,357 B1 | 4/2002 | Schon et al. |
| 6,371,976 B1 | 4/2002 | Vrzalik et al. |
| 6,382,678 B1 | 5/2002 | Field et al. |
| 6,398,748 B1 | 6/2002 | Wilson |
| 6,405,080 B1 | 6/2002 | Lasersohn et al. |
| 6,406,445 B1 | 6/2002 | Ben-nun |
| 6,440,159 B1 | 8/2002 | Edwards et al. |
| 6,443,498 B1 | 9/2002 | Liao |
| 6,508,831 B1 | 1/2003 | Kushnir |
| 6,547,284 B2 | 4/2003 | Rose et al. |
| 6,551,264 B1 | 4/2003 | Cawley et al. |
| 6,551,347 B1 * | 4/2003 | Elkins ................... A61F 7/0085 165/46 |
| 6,551,348 B1 | 4/2003 | Blalock et al. |
| 6,620,187 B2 | 9/2003 | Carson et al. |
| 6,641,601 B1 | 11/2003 | Augustine et al. |
| 6,645,232 B2 | 11/2003 | Carson |
| 6,660,027 B2 | 12/2003 | Gruszecki et al. |
| D486,870 S | 2/2004 | Mason |
| 6,695,872 B2 | 2/2004 | Elkins |
| 6,699,267 B2 | 3/2004 | Voorhees et al. |
| 6,719,713 B2 | 4/2004 | Mason |
| 6,719,728 B2 | 4/2004 | Mason et al. |
| 6,802,823 B2 | 10/2004 | Mason |
| 6,818,012 B2 | 11/2004 | Ellingboe |
| 6,823,682 B1 | 11/2004 | Jenkins et al. |
| 6,871,878 B2 | 3/2005 | Miros |
| 6,893,414 B2 | 5/2005 | Goble et al. |
| 6,926,311 B2 | 8/2005 | Chang et al. |
| 6,932,304 B1 | 8/2005 | Villamar |
| 6,936,019 B2 | 8/2005 | Mason |
| 6,942,015 B1 | 9/2005 | Jenkins |
| 6,948,501 B2 | 9/2005 | Rastegar et al. |
| 7,008,445 B2 | 3/2006 | Lennox |
| 7,017,213 B2 | 3/2006 | Chisari |
| 7,025,709 B2 | 4/2006 | Riggall |
| 7,059,329 B2 | 6/2006 | Mason et al. |
| 7,060,045 B2 | 6/2006 | Mason et al. |
| 7,060,086 B2 | 6/2006 | Wilson et al. |
| 7,093,903 B2 | 8/2006 | O'Connor et al. |
| 7,107,629 B2 | 9/2006 | Miros et al. |
| 7,108,664 B2 | 9/2006 | Mason et al. |
| 7,117,569 B2 | 10/2006 | Bledsoe |
| 7,125,417 B2 | 10/2006 | Mizrahi |
| 7,141,131 B2 | 11/2006 | Foxen et al. |
| 7,156,054 B1 | 1/2007 | York |
| 7,166,083 B2 | 1/2007 | Bledsoe |
| 7,191,798 B2 | 3/2007 | Edelman et al. |
| 7,198,093 B1 | 4/2007 | Elkins |
| 7,235,059 B2 | 6/2007 | Mason et al. |
| 7,244,239 B2 | 7/2007 | Howard |
| 7,306,568 B2 | 12/2007 | Diana |

(56) References Cited

U.S. PATENT DOCUMENTS

| | | |
|---|---|---|
| 7,308,304 B2 | 12/2007 | Hampton |
| 7,326,196 B2 | 2/2008 | Olsen et al. |
| 7,418,755 B2 | 9/2008 | Bledsoe et al. |
| 7,434,844 B2 | 10/2008 | Kao |
| 7,448,653 B2 | 11/2008 | Jensen et al. |
| 7,479,122 B2 | 1/2009 | Ceriani et al. |
| 7,485,103 B2 | 2/2009 | Mason et al. |
| 7,490,620 B2 | 2/2009 | Tesluk et al. |
| 7,500,957 B2 | 3/2009 | Bledsoe |
| 7,591,797 B2 * | 9/2009 | Hakonson ............... A61F 5/012 |
| | | 602/13 |
| 7,640,764 B2 | 1/2010 | Gammons et al. |
| 7,658,205 B1 | 2/2010 | Edelman et al. |
| 7,694,693 B1 | 4/2010 | Edelman et al. |
| 7,731,244 B2 | 6/2010 | Miros et al. |
| 7,785,283 B1 | 8/2010 | Bledsoe |
| 7,833,184 B2 | 11/2010 | Chiodo et al. |
| 7,837,638 B2 | 11/2010 | Miros et al. |
| 7,864,941 B1 | 1/2011 | Bledsoe et al. |
| 7,871,427 B2 | 1/2011 | Dunbar et al. |
| 7,896,910 B2 | 3/2011 | Schirrmacher et al. |
| 7,908,692 B2 | 3/2011 | Lange |
| 7,914,563 B2 | 3/2011 | Mason et al. |
| 7,959,588 B1 | 6/2011 | Wolpa |
| 7,988,653 B2 | 8/2011 | Fout et al. |
| 8,016,779 B2 | 9/2011 | Brown et al. |
| 8,052,628 B1 | 11/2011 | Edelman et al. |
| 8,066,752 B2 | 11/2011 | Hamilton et al. |
| 8,109,273 B2 | 2/2012 | Golden et al. |
| 8,182,521 B2 | 5/2012 | Kane et al. |
| 8,216,163 B2 | 7/2012 | Edelman |
| 8,216,290 B2 | 7/2012 | Shawver et al. |
| 8,216,398 B2 | 7/2012 | Bledsoe et al. |
| 8,226,698 B2 | 7/2012 | Edelman et al. |
| 8,251,932 B2 | 8/2012 | Fout |
| 8,251,936 B2 | 8/2012 | Fout et al. |
| 8,273,045 B2 | 9/2012 | Ceriani |
| 8,277,403 B2 | 10/2012 | Ceriani et al. |
| 8,328,742 B2 | 12/2012 | Bledsoe |
| 8,414,512 B2 | 4/2013 | Foul |
| 8,419,670 B2 | 4/2013 | Downing |
| 8,425,579 B1 | 4/2013 | Edelman et al. |
| 8,444,581 B1 | 5/2013 | Maxon-Maldonado et al. |
| 8,512,263 B2 | 8/2013 | Gammons |
| 8,597,217 B2 | 12/2013 | Lowe et al. |
| 8,613,762 B2 | 12/2013 | Bledsoe |
| 8,715,330 B2 | 5/2014 | Lowe et al. |
| 9,132,057 B2 | 9/2015 | Wilford et al. |
| 9,510,994 B2 * | 12/2016 | Wilford ............... A61F 7/02 |
| 9,615,967 B2 * | 4/2017 | Lowe ............... A61H 9/0092 |
| 2001/0018604 A1 | 8/2001 | Elkins |
| 2001/0034545 A1 | 10/2001 | Elkins |
| 2001/0034546 A1 | 10/2001 | Elkins |
| 2001/0039439 A1 | 11/2001 | Elkins et al. |
| 2002/0019657 A1 | 2/2002 | Elkins |
| 2002/0026226 A1 | 2/2002 | Ein |
| 2002/0032473 A1 | 3/2002 | Kushnir et al. |
| 2002/0041621 A1 | 4/2002 | Fanes et al. |
| 2002/0058975 A1 | 5/2002 | Bieberich |
| 2002/0082668 A1 | 6/2002 | Ingman |
| 2002/0093189 A1 | 7/2002 | Krupa |
| 2002/0108279 A1 | 8/2002 | Hubbard et al. |
| 2003/0060761 A1 | 3/2003 | Evans et al. |
| 2003/0196352 A1 | 10/2003 | Bledsoe et al. |
| 2004/0064170 A1 | 4/2004 | Radons et al. |
| 2004/0064171 A1 | 4/2004 | Briscoe et al. |
| 2004/0068309 A1 | 4/2004 | Edelman |
| 2004/0158303 A1 | 8/2004 | Lennox et al. |
| 2004/0167594 A1 | 8/2004 | Elkins |
| 2004/0210283 A1 | 10/2004 | Rose et al. |
| 2004/0225341 A1 | 11/2004 | Schock et al. |
| 2004/0243202 A1 | 12/2004 | Lennox |
| 2005/0027173 A1 | 2/2005 | Briscoe et al. |
| 2005/0065581 A1 | 3/2005 | Fletcher et al. |
| 2005/0070828 A1 * | 3/2005 | Hampson ............ A61H 9/0092 |
| | | 601/152 |
| 2005/0126578 A1 | 6/2005 | Garrison et al. |
| 2005/0131324 A1 | 6/2005 | Bledsoe |
| 2005/0136213 A1 | 6/2005 | Seth et al. |
| 2005/0143796 A1 | 6/2005 | Augustine |
| 2005/0143797 A1 | 6/2005 | Parish |
| 2006/0058858 A1 | 3/2006 | Smith |
| 2006/0069418 A1 | 3/2006 | Schock et al. |
| 2006/0144557 A1 | 7/2006 | Koscheyev et al. |
| 2006/0190062 A1 | 8/2006 | Worthen |
| 2006/0200057 A1 | 9/2006 | Sterling |
| 2006/0287697 A1 | 12/2006 | Lennox |
| 2007/0038167 A1 * | 2/2007 | Tabron ............... A61F 5/012 |
| | | 601/152 |
| 2007/0060987 A1 | 3/2007 | Grahn et al. |
| 2007/0068651 A1 | 3/2007 | Gammons et al. |
| 2007/0108829 A1 | 5/2007 | Lehn et al. |
| 2007/0118194 A1 | 5/2007 | Mason et al. |
| 2007/0118965 A1 | 5/2007 | Hoffman |
| 2007/0157931 A1 | 7/2007 | Parker et al. |
| 2007/0161932 A1 | 7/2007 | Pick et al. |
| 2007/0161933 A1 | 7/2007 | Ravikumar |
| 2007/0167895 A1 | 7/2007 | Gramza et al. |
| 2007/0191918 A1 | 8/2007 | MacHold et al. |
| 2007/0282230 A1 | 12/2007 | Valderrabano et al. |
| 2008/0000474 A1 | 1/2008 | Jochle et al. |
| 2008/0058911 A1 | 3/2008 | Parish et al. |
| 2008/0065172 A1 | 3/2008 | Magdych |
| 2008/0067095 A1 | 3/2008 | Mueller |
| 2008/0097560 A1 | 4/2008 | Radziunas et al. |
| 2008/0097561 A1 | 4/2008 | Melsky et al. |
| 2008/0132816 A1 | 6/2008 | Kane et al. |
| 2008/0132976 A1 | 6/2008 | Kane et al. |
| 2008/0161891 A1 | 7/2008 | Pierre et al. |
| 2008/0234788 A1 | 9/2008 | Wasowski |
| 2008/0249593 A1 | 10/2008 | Cazzini et al. |
| 2008/0269852 A1 | 10/2008 | Lennox et al. |
| 2008/0275534 A1 | 11/2008 | Noel |
| 2008/0283426 A1 | 11/2008 | Primer et al. |
| 2009/0005841 A1 | 1/2009 | Schirrmacher et al. |
| 2009/0018623 A1 | 1/2009 | Levinson et al. |
| 2009/0038195 A1 | 2/2009 | Riker et al. |
| 2009/0062703 A1 * | 3/2009 | Meyer ............... A61H 9/0078 |
| | | 602/13 |
| 2009/0062890 A1 | 3/2009 | Ugajin et al. |
| 2009/0069731 A1 | 3/2009 | Parish et al. |
| 2009/0183410 A1 | 7/2009 | Tursso et al. |
| 2010/0006631 A1 | 1/2010 | Edwards |
| 2010/0076531 A1 | 3/2010 | Beran et al. |
| 2010/0089896 A1 | 4/2010 | Bart |
| 2010/0094187 A1 | 4/2010 | Murinson et al. |
| 2010/0137951 A1 | 6/2010 | Lennox et al. |
| 2010/0137953 A1 | 6/2010 | Stein |
| 2010/0139294 A1 | 6/2010 | Lowe et al. |
| 2010/0145421 A1 | 6/2010 | Tomlinson et al. |
| 2010/0161013 A1 | 6/2010 | Heaton |
| 2010/0217349 A1 | 8/2010 | Fahey |
| 2010/0241120 A1 | 9/2010 | Bledsoe et al. |
| 2011/0004132 A1 | 1/2011 | Cook |
| 2011/0028873 A1 | 2/2011 | Miros et al. |
| 2011/0040359 A1 | 2/2011 | Harris et al. |
| 2011/0046700 A1 | 2/2011 | McDonald et al. |
| 2011/0087142 A1 | 4/2011 | Ravikumar et al. |
| 2011/0098792 A1 | 4/2011 | Lowe et al. |
| 2011/0106023 A1 | 5/2011 | Lowe |
| 2011/0152982 A1 | 6/2011 | Richardson |
| 2011/0152983 A1 | 6/2011 | Schirrmacher et al. |
| 2011/0172749 A1 | 7/2011 | Christensen et al. |
| 2011/0307038 A1 | 12/2011 | Stiehr |
| 2012/0010546 A1 | 1/2012 | Sotereanos et al. |
| 2012/0028764 A1 | 2/2012 | Miller |
| 2012/0143111 A1 | 6/2012 | Bledsoe et al. |
| 2012/0172955 A1 | 7/2012 | Dewaegenaere |
| 2012/0179084 A1 | 7/2012 | Lipshaw et al. |
| 2012/0233736 A1 | 9/2012 | Tepper et al. |
| 2012/0245483 A1 | 9/2012 | Lundqvist |
| 2012/0288848 A1 | 11/2012 | Latham et al. |
| 2012/0330199 A1 | 12/2012 | Lurie et al. |

(56) References Cited

U.S. PATENT DOCUMENTS

| | | |
|---|---|---|
| 2012/0330202 A1 | 12/2012 | Flick |
| 2013/0006154 A1 | 1/2013 | Lowe |
| 2013/0006335 A1 | 1/2013 | Lowe |
| 2013/0012847 A1 | 1/2013 | Lowe et al. |
| 2013/0013033 A1 | 1/2013 | Lowe |
| 2013/0090683 A1 | 4/2013 | Schock |
| 2013/0123890 A1 | 5/2013 | Latham |
| 2013/0165847 A1 | 6/2013 | Scarpaci et al. |
| 2013/0190553 A1 | 7/2013 | Wong et al. |
| 2013/0245519 A1 | 9/2013 | Edelman et al. |
| 2013/0245729 A1 | 9/2013 | Edelman et al. |
| 2013/0296981 A1 | 11/2013 | Saggers |
| 2014/0074198 A1 | 3/2014 | Bledsoe |
| 2014/0078086 A1 | 3/2014 | Bledsoe et al. |
| 2014/0222121 A1 | 8/2014 | Spence et al. |
| 2014/0236256 A1 | 8/2014 | Rossing |
| 2014/0243939 A1 | 8/2014 | Lowe et al. |
| 2014/0277301 A1 | 9/2014 | Varga et al. |
| 2014/0316314 A1 | 10/2014 | Schubert |
| 2015/0150717 A1 | 6/2015 | Lowe et al. |
| 2015/0335468 A1 | 11/2015 | Rose et al. |
| 2015/0374538 A1 | 12/2015 | Rogers |
| 2016/0030234 A1 | 2/2016 | Lofy et al. |
| 2016/0038336 A1 | 2/2016 | Schirrmacher et al. |
| 2016/0128865 A1 | 5/2016 | Lowe |
| 2016/0166428 A1 | 6/2016 | Hilton et al. |
| 2018/0271688 A1 | 9/2018 | Miros et al. |

FOREIGN PATENT DOCUMENTS

| | | |
|---|---|---|
| CN | 2880025 Y | 3/2007 |
| CN | 201001805 Y | 1/2008 |
| CN | 201070419 Y | 6/2008 |
| CN | 101524301 A | 9/2009 |
| DE | 3343664 C1 | 3/1985 |
| DE | 29716336 U1 | 1/1998 |
| DE | 29716338 U1 | 1/1998 |
| EP | 0344949 A2 | 12/1989 |
| EP | 0412708 A1 | 2/1991 |
| EP | 0535830 A1 | 4/1993 |
| EP | 0861651 B1 | 4/2002 |
| EP | 1329676 A1 | 7/2003 |
| EP | 1393751 A1 | 3/2004 |
| EP | 1972312 A2 | 9/2008 |
| FR | 819022 A | 10/1937 |
| IT | 330552 | 10/1935 |
| JP | 08-229061 A | 9/1996 |
| JP | 2000288007 A | 10/2000 |
| KR | 20-0153967 | 8/1999 |
| KR | 100654317 B1 | 12/2006 |
| NL | 2011288 C | 8/2013 |
| WO | WO92/13506 A1 | 8/1992 |
| WO | WO92/15263 A1 | 9/1992 |
| WO | WO94/09732 A1 | 5/1994 |
| WO | WO96/26693 A1 | 9/1996 |
| WO | WO98/07397 A1 | 2/1998 |
| WO | WO99/44552 A1 | 9/1999 |
| WO | WO00/23016 A1 | 4/2000 |
| WO | WO00/55542 A1 | 9/2000 |
| WO | WO00/67685 A1 | 11/2000 |
| WO | WO02/19954 A2 | 3/2002 |
| WO | WO02/38091 A1 | 5/2002 |
| WO | WO 03/000079 A2 | 1/2003 |
| WO | WO03/072008 A2 | 9/2003 |
| WO | WO2005/007060 A2 | 1/2005 |
| WO | WO2005/082301 A1 | 9/2005 |
| WO | WO2006/110405 A2 | 10/2006 |
| WO | WO2010/060931 A1 | 6/2010 |
| WO | WO2011/019603 A1 | 2/2011 |

OTHER PUBLICATIONS

U. Jarfelt, O. Ramnäs. Paper presented at: 10th International Symposium on District Heating and Cooling, 2006; Chalmers University of Technology. Accessed Mar. 13, 2020 (Year: 2006).*

Rubbercal. Neoprene Durometer: Using a Durometer. Rubbercal. https://www.rubbercal.com/sheet-rubber/neoprene-durometer/#bottom. Updated 2019. Accessed Apr. 9, 2020 (Year: 2019).*

U. Jarfelt, O. Ramnäs. Paper presented at: 10th International Symposium on District Heating and Cooling, 2006; Chalmers University of Technology. Accessed Mar. 13, 2020 (Year: 2020).*

Webster Dictionary; Shunt (definition); Merriam-Webster, Inc.; 11 pages; retrieved from the internet (https://www.merriam-webster.com/dictionary/shunt on Apr. 13, 2018.

Lowe et al.; U.S. Appl. No. 15/927,937 entitled Temperature and flow control methods in a thermal therapy device, filed Mar. 21, 2018.

Hilton et al., U.S. Appl. No. 16/178,467 entitled "Integrated multisectional heat exchanger," filed Nov. 1, 2018.

BioCompression Systems, Inc. (Moonachie, NJ); Product literature for Sequential Circulators; 15 pgs.; Oct. 1997.

Cothera LLC; VPULSE System Users Manual; 100149 Rev E; ©2013; 18 pgs. (manual rev. dated Jul. 2013).

Johns Hopkins Medicine; Patient guide to UCL injuries of the elbow (ulnar collateral ligament); 8 pages; Sep. 3, 2010; retrieved from the internet Apr. 20, 2015 (http:/www.hopkinsortho.org/ucl.html).

Van Eps et al.; Distal limb cryotherapy for the prevention of acute laminitis; Clin Tech Equine Pract; vol. 3; pp. 64-70; Mar. 2004.

Van Eps et al.; Equine laminitis: cryotherapy reduces the severity of the acute lesion; Equine Veterinary Journal; vol. 36; No. 3; pp. 255-260; Apr. 2004.

* cited by examiner

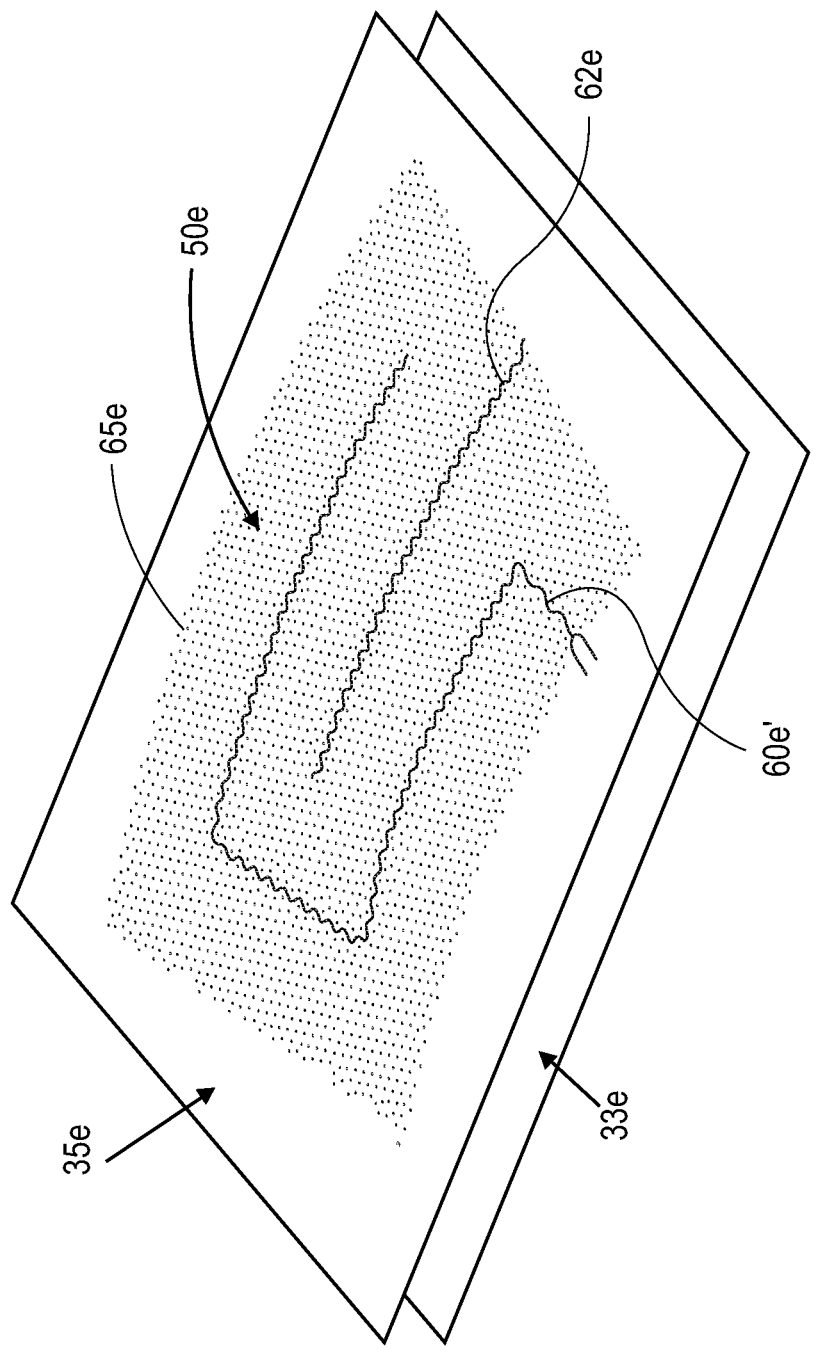

REINFORCED THERAPEUTIC WRAP AND METHOD

CROSS REFERENCE TO RELATED APPLICATIONS

This application is a continuation of U.S. application Ser. No. 14/095,954, filed Dec. 3, 2013, titled "REINFORCED THERAPEUTIC WRAP AND METHOD," now U.S. Pat. No. 9,615,967, which is a continuation-in-part of U.S. application Ser. No. 12/982,266, filed Dec. 30, 2010, titled "REINFORCED THERAPEUTIC WRAP AND METHOD," now U.S. Pat. No. 8,597,217, both of which are herein incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to therapy of an animate body, and more particularly a therapeutic wrap of the type having circulating fluid to provide cooling, heating, and/or compression to a human or animal body part.

BACKGROUND

It is now common to apply cold and compression to a traumatized area of a human body to facilitate healing and prevent unwanted consequences of the trauma. In fact, the acronym RICE (Rest, Ice, Compression and Elevation) is now used by many.

Typically thermally-controlled therapy involves cold packing with ice bags or the like to provide deep core cooling of a body part. Therapy often involves conventional therapy wraps with a fluid bladder for circulating a cooled heat exchange medium. Elastic wraps are often applied over the therapy wrap to provide compression.

More recently therapy wraps including a pair of compliant bladders to contain fluids have been disclosed. The therapy wrap typically has a compliant bladder for containing a circulating heat exchange liquid alone or in combination with a compressive bladder which overlays the compliant bladder for pressing the bladder against the body part to be subjected to heat exchange. In general, the body heat exchanging component(s) of such an apparatus include a pair of layers defining a flexible fluid bladder through which a liquid is circulated. The structure embodying both the liquid bladder and compressive bladder component is often referred to as a "wrap." The liquid fed to the wrap is maintained at a desired temperature by passing the liquid through a heat exchanging medium such as an ice bath or a refrigeration unit. One such system is disclosed, for example, in U.S. Pat. No. 6,178,562 to Elkins, the disclosure of which is herein incorporated for all purposes by reference.

Therapy wraps can be used to provide therapy in a variety of contexts whether for humans, equine animals, dogs, or any other mammal. Therapy wraps can be shaped and designed for application to a variety of anatomical body parts such as a hoof, a shoulder, a knee, a leg, a head, and more.

A problem occurs when applying the wrap to such complex shapes. Bending of the wrap in one or more directions can cause localized kinking or buckling in the bladder. In some cases, one or more fluid pathways becomes crimped or completely occluded, thereby inhibiting fluid flow and operation. This type of kinking generally occurs because of the inability of the material to conform to the complex shape of the anatomical part to which it is applied. It is believed that, in part, the material collapses and/or bunches when wrapped around tight radiuses.

Kinking may also occur with therapeutic wraps having two bladders fixed together. As the wrap is bent or folded, the bladders cannot shear or move past one another. This type of kinking is sometimes referred to as buckling.

It is believed that the above and other types of kinking conditions are further exacerbated by the compressive force on the compliant fluid bladder. The compressive force promotes further kinking after the walls of the bladder begin to kink.

Kinking leads to several performance problems. Kinking of the fluidic channels can lead to cool spots that are uncomfortable for the user and render heat transfer inconsistent. Kinking can also undesirably increase backpressure in local regions of the fluid bladder. In the case of severe kinking, fluid flow is completely stopped through a fluid flowpath and heat exchange cannot occur.

To date, the effects of kinking in the context of therapy wraps have not been adequately explored. One existing wrap design provides a fluid bladder with a plurality of spot welds (also referred to as "dots") to reduce "ballooning." An example of such a fluid bladder is disclosed in U.S. Pat. No. 6,695,872 to Elkins. The dots also effectively split the fluid pathway into a plurality of fluidic channels. The conventional use of dots is limited in that such fluid bladders experience an undesirably large number of kink failures and other failure modes during use, especially when applied to complex body parts and/or in compression from a pressure bladder.

The risk of kinking may be reduced by increasing the rigidity of the materials forming the bladder. Among the many limitations of this approach, increasing the rigidity of the materials detrimentally requires a trade-off between conformability of the wrap and kink resistance.

There remains the need for providing improved wraps with good heat exchange performance and increased resistance to kinking, in particular when conformed and compressed to complex shapes or bent around a tight radius curve. Even if a complete blockage of the fluidic channel does not occur, an undesirable reduction of fluid flow generally decreases wrap performance.

There is the need for a wrap that is conformable to a complex anatomical shape and provides efficient heat transfer over the treatment surface under compressive force. There is a need for a wrap that reduces the risk of kinking or buckling. There is the need to provide a wrap that improves patient comfort.

There is the need for a therapeutic wrap that overcomes the above and other problems. There remains a need to provide improved temperature-controlled therapy apparatus and methods for their use.

SUMMARY OF THE DISCLOSURE

The present invention involves improvements in heat transfer therapy apparatus and avoids disadvantages in the prior art.

Various aspects of the invention are directed to a therapy wrap with improved kink resistance. In various embodiments, the therapy wrap is selectively reinforced for improved kink resistance in only a portion of the wrap. In various embodiments, the wrap has a decreased kink radius. In various embodiments, one or more selected regions are modified to have an increased kink resistance. Various aspects of the invention are directed to a therapy wrap for providing heating or cooling to an anatomical body part requiring treatment.

Various aspects of the invention are directed to a therapy wrap including a flexible fluid bladder for containing a heat exchange medium, the fluid bladder including an inlet, an outlet, a fluid flowpath connecting the inlet and the outlet, and a plurality of attachment points connecting walls of the bladder and defining a plurality of fluidic channels in the flowpath; and a gas pressure bladder for applying a compressive force to a portion of the fluid bladder in contact with the body part. The attachment points are positioned and dimensioned to increase resistance to kinking of the fluid bladder.

Various aspects of the invention are directed to a therapy wrap for providing heating or cooling to an anatomical body part, the wrap including a flexible fluid bladder for containing a heat exchange medium, the fluid bladder including an inlet, an outlet, a fluid flowpath connecting the inlet and the outlet, and a plurality of attachment points connecting walls of the bladder and defining a plurality of fluidic channels in the flowpath; and a gas pressure bladder overlaying the fluid bladder for applying a compressive force to a portion of the fluid bladder in contact with the body part. A portion of the plurality of attachment points may be positioned and dimensioned to increase resistance to kinking of the fluid bladder in a region of the fluid bladder prone to kinking during use.

In various embodiments, the attachment points are dots formed by spot welding. In various embodiments, the attachment points are circular-shaped and have an essentially equal diameter. In various embodiments, the attachment points have a diameter between about 0.15 inch and about 0.2 inch. The attachment points may a diameter being between about 0.15 inch and about 0.35 inch. The attachment points may have an average center-to-center spacing between adjacent attachment points between about 0.35 inch and about 0.75 inch. The attachment points may have an average center-to-center spacing between adjacent attachment points between about 0.35 inch and about 0.5 inch. The attachment points may have an average edge-to-edge spacing between adjacent attachment points between about 0.2 inch and about 0.5 inch. The attachment points may have an average edge-to-edge spacing between adjacent attachment points between about 0.2 inch and about 0.25 inch.

In various embodiments, a ratio of the fluid volume of the fluid bladder to a treatment area of the fluid bladder is between about $1 L/m^2$ and about $3.5 L/m^2$ at 10 psi. The ratio of the fluid volume of the fluid bladder to a treatment area of the fluid bladder may be between about $1 L/m^2$ and about $1.5 L/m^2$ at 10 psi. The ratio of the fluid volume of the fluid bladder to a treatment area of the fluid bladder may be between about $1.2 L/m^2$ and about $3 L/m^2$ at 20 psi. The ratio of the fluid volume of the fluid bladder to a treatment area of the fluid bladder may be at least about $1 L/m^2$ at 5 psi.

In various embodiments, the fluidic channels are dimensioned to increase kink resistance. In various embodiments, the average fluidic channel cross-sectional area in a kink-resistant region is about $0.02 inch^2$, and more preferably $0.0254 inch^2$. In various embodiments, the average fluidic channel cross-sectional area in a kink-resistant region is between about $10 mm^2$ and about $40 mm^2$, more preferably between about $15 mm^2$ and about $25 mm^2$.

In various embodiments, the compressive force is in a range from about 0.25 psi to about 3 psi. In various embodiments, the compressive force is in a range from 0 psi to about 5 psi.

Various aspects of the invention are directed to a therapy wrap for providing treatment to an anatomical body part, the wrap including a flexible fluid bladder for containing a heat exchange medium and including an inlet, an outlet, and a fluid flowpath connecting the inlet and the outlet; a gas pressure bladder overlaying the fluid bladder for applying a compressive force to a portion of the heat exchanger in contact with the body part; and a kink reducer for selectively increasing kink resistance of the fluid bladder in a kink-resistant zone subject to the compressive force, the kink-resistant zone being positioned only along a portion of the at least one fluidic channel spaced from the inlet and outlet. Various aspects of the invention are directed to a therapy wrap conformable to an anatomical body part including a flexible heat exchanger for containing a heat exchange medium and including an inlet, an outlet, and a fluid flowpath connecting the inlet and the outlet; a gas pressure bladder for applying a compressive force to a portion of the heat exchanger in contact with the body part; and a kink reducer for selectively increasing kink resistance of the heat exchanger in a kink-resistant zone subject to the compressive force. In various embodiments, the kink reducer is a member selected from the group consisting of a plurality of dot connections, a discrete reinforcement member, and a combination of the same. In various embodiments, the kink-resistant zone being positioned only along a portion of the at least one fluidic channel distally from the inlet and outlet. In various embodiments, the kink-resistant zone being positioned only along a portion of the at least one fluidic channel spaced from the inlet and outlet.

In various embodiments, the wrap further includes a plurality of circular-shaped attachment points connecting opposite walls of the heat exchanger interiorly of a periphery of the heat exchanger and defining a plurality of fluidic channels in the flowpath. The kink reducer may include attachment points having a variable spacing between adjacent points positioned and dimensioned to increase resistance to local kinking of the heat exchanger. In various embodiments, the fluid bladder is formed of one of polyurethane, nylon, and a combination of the same.

In various embodiments, an average spacing between adjacent attachment points in the kink-resistant zone may be greater than an average spacing between adjacent attachment points in the remainder of the heat exchanger. The average spacing in the kink-resistant zone may be at least 20% greater than the average spacing in the remainder of the heat exchanger. The average spacing in the kink-resistant zone may be at least 25%, at least about 30%, at least about 40%, at least about 50%, or at least about 75% greater than the average spacing in the remainder of the heat exchanger.

In various embodiments, an average edge-to-edge spacing between adjacent attachment points in the kink-resistant zone is between about 0.2 inch and about 0.5 inch.

In various embodiments, the attachment points are spot welds. In various embodiments, the attachment points are dots.

In various embodiments, the plurality of attachment points in the kink-resistant zone are positioned in a non-linear pattern.

In various embodiments, the plurality of fluidic channels in the kink-resistant zone have a cross-sectional area greater than a cross-sectional area of the fluidic channels in the remainder of the fluid bladder.

In various embodiments, the kink-resistant zone has a tensile bending strength increased by at least 20%, at least 30%, at least 40%, at least 50%, at least 75%, or at least 100%. In various embodiments, the kink-resistant zone has a tensile bending strength at least 75% greater than the remainder of the heat exchanger.

In various embodiments, the wrap includes a selectively reinforced dot pattern to increase the local tensile strength by at least about 10%, and more preferably at least about 20%, at least about 50%, at least about 75%, at least about 100%, or at least about 150%. In various embodiments, the selectively reinforced dot pattern is configured to reduce the occurrence of kinking during use by at least about 10%, and more preferably at least about 20%, at least about 50%, or at least about 75%.

In various embodiments, the heat exchanger is a fluid bladder for containing cooled water and the gas pressure bladder is for containing pressurized air. In various embodiments, when the fluid bladder is filled with water at 19 psi, the fluidic channels in the kink-resistant zone provide at least about 10 pounds of resistive force when displaced by about 0.1 inches over about a 2-inch diameter area. In various embodiments, the fluidic channels provide at least about 5 pounds when displaced by about 0.13 inch, at least about 11 pounds when displaced by about 0.11 inch, at least about 17 pounds when displaced by about 0.1 inch, at least about 22 pounds when displaced by about 0.09 inch, and/or at least about 27 pounds when displaced by about 0.08 inch.

In various embodiments, a ratio of the fluid volume of the heat exchanger to a treatment area of the heat exchanger is between is between about 1 L/m2 and about 3.5 L/m2 when the fluid in the heat exchanger is at 10 psi.

In various embodiments, the wrap includes a check valve or flow restrictor to maintain backpressure in the fluid bladder.

In various embodiments, the kink reducer comprises a discrete reinforcement member to impart significantly increased resistance to kinking in the kink-resistant zone relative to the remainder of the heat exchanger. In various embodiments, the kink reducer comprises a discrete reinforcement member coupled to the fluid bladder in the kink-resistant zone. In various embodiments, the reinforcement member increases the tensile bending strength of the kink-resistant zone by at least 75% relative to the remainder of the heat exchanger. In various embodiments, the reinforcement member increases the tensile bending strength of the kink-resistant zone by at least 25%, by at least 50%, or by at least 75% relative to the remainder of the heat exchanger. The reinforcement member may be a rigid body having a shape selected from a wire, an exoskeleton, a ribbon, and a sheet.

In various embodiments, the reinforcement member is a rigid member selected from the group consisting of a wire, an exoskeleton, a ribbon, a sheet, and a combination of the same.

In various embodiments, the wrap includes a plurality of dot connections and a discrete reinforcement member. The dot connections may be formed in a region overlapping the reinforcement member. The reinforcement member may overlap the dot connections. The reinforcement member and dot connections may be positioned in the same region.

In various embodiments, the reinforcement member is positioned within the gas pressure bladder. In various embodiments, a position of the kink-resistant zone corresponds to an anatomical joint of a patient to be treated. The body part may be a back of a joint. The kink-resistant zone may correspond to one of a back of a knee or a back of an elbow. A position of the kink zone may correspond to a narrowed region of the common border. In various embodiments, the heat exchanger and gas pressure bladder are integrally connected and fluidly separated by a common wall.

In various embodiments, the kink reducer is a member selected from attachment points, a discrete reinforcement member, and a combination of the same as described herein. In various embodiments, the kink-reducer is a pre-tensioned region manufactured as described herein. The kink reducer may be modified to achieve a desired variation in kink resistance.

Various aspects of the invention are directed to a therapy wrap for providing treatment to an anatomical body part, the wrap including a first outer layer of flexible material; a second outer layer of flexible material; a middle layer between the first and second layers of flexible material; a plurality of connections joining the first and middle layers to form a fluid bladder, the plurality of connections comprising dots and fences defining a plurality of fluidic channels in the fluid bladder; the fluid bladder comprising a first zone and a second zone of dots; and a border joining the second outer layer and middle layer to form a gas pressure bladder. The dots in the second zone may be positioned and configured to increase a bending strength of the second zone relative to the first zone when the wrap is in use. A portion of the dots in the fluid bladder may be positioned and configured to increase a bending strength of a local region relative to the remainder of the wrap when it is in use. Various aspects of the invention are directed to a therapy wrap conformable to an anatomical body part including a first outer layer of flexible material; a second outer layer of flexible material; a middle layer between the first and second layers of flexible material; and a border joining the second outer layer and middle layer to form a gas pressure bladder.

In various embodiments, a plurality of connections join the first and middle layers to form a fluid bladder. The plurality of connections may include dots and fences defining a plurality of fluidic channels in the fluid bladder. In various embodiments, the fluid bladder includes a first zone and a second zone of dots; the dots in the second zone increase a bending strength of the second zone relative to the first zone when the wrap is in use.

In various embodiments, the plurality of connections are welds between the first outer layer and middle layer.

In various embodiments, the dots in the second zone have an average edge-to-edge spacing between about 0.2 inch and about 0.5 inch. The dots in the second zone may have an essentially equal diameter, the diameter of the dots being between about 0.15 inch and about 0.35 inch.

In various embodiments, the plurality of connections joining the first and middle layer include a common border along a periphery of the first and middle layer and a plurality of fences interiorly of the common border defining a fluid flowpath, the plurality of dots dividing the fluid flowpath into the plurality of fluidic channels.

In various embodiments, in the second zone, the dots inward of the border are larger than those adjacent the border. In various embodiments, in the second zone, the dots have a variable diameter.

In various embodiments, the dots are attachment points configured and dimensioned as described herein.

Various aspects of the invention are directed to a therapy wrap as described herein.

Various aspects of the invention are directed to a method of forming a therapy wrap as described herein.

Various aspects of the invention are directed to a method of forming a flexible wrap for thermal therapy, the method including joining a first layer of flexible material to a second layer of flexible material to form at least one interior fence, the at least one fence defining at least one fluid pathway between the first layer and second layer; and joining the first layer to the second layer to form a plurality of dots defining a plurality of fluidic channels in the at least one fluid pathway, a portion of the plurality of dots corresponding to a kink-prone region of the wrap and the dots in the portion sized and shaped to increase resistance to kinking in the kink-prone region. In various embodiments, the joining to form the multi-chamber wrap is performed simultaneously with the forming of the at least one interior fence and the forming of the dots. In various embodiments, the forming of the at least one fence comprises forming the at least one fence to extend through the second layer and third layer.

Various aspects of the invention are directed to a method of forming a flexible wrap for thermal therapy and conformable to an anatomical body part, the method including forming a plurality of connections joining a first layer of flexible material and a second layer of flexible material; joining a third layer of flexible material, the second layer of flexible material, and the first layer of flexible material along a peripheral border; and forming at least one fence and a plurality of dots between the first layer and the second layer and interiorly of the peripheral border. The at least one fence defines at least one fluid pathway between the first layer and second layer. The plurality of dots define a plurality of fluidic channels in the at least one fluid pathway. In various embodiments, the forming of the dots includes forming a dot matrix in a first zone and a dot matrix in a second zone along the at least one fluid pathway, the second zone corresponding to a kink-prone region of the wrap, the dot matrix in the second zone to increase resistance to kinking within a localized area of the dots. In various embodiments, the dot matrix in the second zone is formed without any linear arrangement. In various embodiments, the dot matrix in the second zone is formed in a non-linear arrangement.

In various embodiments, the forming of the plurality of dots comprises forming a repeating pattern of essentially aligned dots in the first zone. The forming of the at least one fence may include forming the at least one fence to extend between the second layer and third layer.

In various embodiments, the forming of the plurality of dots is accomplished by increasing a spacing between adjacent dots in the second zone relative to a spacing between adjacent dots in the first zone.

In various embodiments, the plurality of dots in the second zone have an essentially equal diameter, the diameter of the dots being between about 0.15 inch and about 0.35 inch.

In various embodiments, the kink-prone region corresponds to an anatomical joint. The kink-prone region may correspond to a narrowed region of the first and second layers.

Various aspects of the invention are directed to a method of forming a heat exchanger, the method including sealing a first layer of flexible material to a second layer of flexible material to form a peripheral border and a fluid pathway; and attaching a selective reinforcement layer to the second layer along a portion of the fluid pathway corresponding to a kink-prone region.

In various embodiments, the method includes attaching the selective reinforcement layer along another portion of the fluid pathway. The reinforcement layer may include a substrate carrying a rigid structural member. The structural member may be a substantially flat batten formed of stiffened urethane. The structural member may be attached only along the portion of the fluid pathway corresponding to the kink-prone region. The reinforcement layer may be positioned on an opposite side of the second layer from the first layer.

In various embodiments, the method further includes attaching another reinforcement layer to the second layer along a different portion of the fluid pathway than the reinforcement layer. In various embodiments, the another reinforcement layer and reinforcement layer are integrally formed. The another reinforcement layer and reinforcement layer may be spaced from an inlet and an outlet of the fluid pathway.

Various aspects of the invention are directed to a method of making a heat exchanger conformable to a complex shape, the method including forming a first layer of a flexible material; forming a second layer of a flexible material; sealing the first layer to the second layer along a common border; securing the first layer to the second layer interiorly of said border to define at least one fluidic channel in a first region; securing the first layer to the second layer interiorly of said border to define another fluidic channel in a second region; and attaching a selective reinforcement layer only along the another fluidic channel in the second region.

In various embodiments, the reinforcement layer comprises a substrate carrying a rigid structural member. The structural member may be a substantially flat batten. The structural member may be formed of stiffened urethane.

In various embodiments, the reinforcement layer is positioned on an opposite side of the second layer from the first layer.

Various aspects of the invention are directed to a method of forming a therapy wrap, the method including tensioning a member selected from the group consisting of a first layer of flexible material, a second layer of flexible material, and a combination of the same; during the tensioning, sealing the second layer over the first layer along a common border to form a bladder.

In various embodiments, the method further includes, after the sealing, releasing the formed bladder. The tensioning may be performed in only a kink-prone region of the selected member.

In various embodiments, the method includes sealing a third layer of flexible material over the second layer along the common border to form another bladder, the another bladder attached to and overlaying the bladder. The sealing to form the first bladder or sealing to form the second bladder may include forming a plurality of interior control fences extending through the second layer and defining at least one fluid flowpath in the bladder and the another bladder. The sealing of the first layer to the second layer and the sealing of the second layer to the third layer may be performed substantially simultaneously.

In various embodiments, the tensioning includes heating the selected member. In various embodiments, the tensioning includes stretching the selected member.

Various aspects of the invention are directed to a method of making a therapy wrap which is conformable to an anatomical joint, the method including forming a first outer layer of a flexible material; forming a middle layer of flexible material overlaying the first outer layer; pre-tensioning at least one of the first outer layer and middle layer; and while the kink-resistant zone remains pre-tensioned, sealing the first outer layer to the middle layer along a common peripheral border to form a fluid bladder.

In various embodiments, the pre-tensioning of at least one of the first outer layer and the middle layer is performed in only a selected kink-resistant zone of the layers. In various embodiments, the pre-tensioning is performed to a selected region positioned remotely from the inlet and the outlet.

In various embodiments, the method includes forming a second outer layer of a flexible material overlaying the middle layer; and sealing the second outer layer to the middle layer to form a gas pressure bladder.

The kink-resistant zone may correspond to a location of an apex of the anatomical joint requiring treatment.

In various embodiments, the sealing to form a fluid bladder includes forming a plurality of control fences extending through the first outer layer, the middle layer, and the second outer layer, interiorly of said border, to form at least one fluid flowpath in the fluid bladder and the gas pressure bladder. The sealing of the first outer layer to the middle layer and the sealing of the second outer layer to the middle layer may be performed essentially simultaneously.

In various embodiments, the pre-tensioning comprises heating the at least one of the first outer layer and the middle layer prior to the sealing.

In various embodiments, a therapy wrap for providing heating or cooling to an anatomical body part is provided. The wrap may include a flexible fluid bladder for containing a heat exchange medium, the fluid bladder including an inlet, an outlet, and a fluid flowpath connecting the inlet and the outlet; a gas pressure bladder overlaying the fluid bladder for applying a compressive force to a portion of the fluid bladder in contact with the body part; and a reinforcement member disposed within the gas pressure bladder at one or more kink prone regions of the gas pressure bladder, wherein the reinforcement member reduces kinking at the one or more kink prone regions of the gas pressure bladder.

In some embodiments, the reinforcement member is a made from a porous material. In some embodiments, the porous material has an open cell foam structure that is gas permeable.

In some embodiments, the reinforcement member has a hole and a weld that passes through the hole that secures the reinforcement member within the gas pressure bladder. In some embodiments, the reinforcement member is donut shaped.

In some embodiments, the reinforcement member is secured to the gas pressure bladder with an adhesive.

In some embodiments, the therapy wrap further includes a plurality of attachment points connecting walls of the bladder and defining a plurality of fluidic channels in the flow path. In some embodiments, the reinforcement member is secured within the gas pressure bladder with a weld that is aligned with one of the attachment points.

In some embodiments, the size and shape of the reinforcement member is defined at least in part by one or more of the plurality of attachment points within the bladder.

In some embodiments, the reinforcement member is curvilinear. In some embodiments, the reinforcement member is circular or oval.

In some embodiments, the reinforcement member is rectilinear. In some embodiments, the reinforcement member is square or rectangular.

In some embodiments, the size and shape of the reinforcement member is defined at least in part by a perimeter of the gas pressure bladder. In some embodiments, the size and shape of the reinforcement member is defined at least in part by one or more interior fences disposed within the fluid bladder or gas pressure bladder.

In some embodiments, the reinforcement member is made from an insulating material. In some embodiments, reinforcement member is adhered to a wall of the gas pressure bladder that is adjacent or shared with the fluid bladder.

In some embodiments, a therapy wrap for providing treatment to an anatomical body part is provided. The wrap may include a gas pressure bladder for applying a compressive force to the body part; and a reinforcement member disposed within the gas pressure bladder at one or more kink prone regions of the gas pressure bladder, wherein the reinforcement member reduces kinking at the one or more kink prone regions of the gas pressure bladder.

In some embodiments, the reinforcement member is a made from a porous material. In some embodiments, the porous material has an open cell foam structure that is gas permeable.

In some embodiments, the reinforcement member has a hole and a weld that passes through the hole that secures the reinforcement member within the gas pressure bladder. In some embodiments, the reinforcement member is donut shaped.

In some embodiments, the reinforcement member is secured to the gas pressure bladder with an adhesive. In some embodiments, the reinforcement member is secured within the gas pressure bladder with one or more welds.

In some embodiments, the reinforcement member is curvilinear. In some embodiments, the reinforcement member is circular or oval.

In some embodiments, the reinforcement member is rectilinear. In some embodiments, the reinforcement member is square or rectangular.

In some embodiments, the size and shape of the reinforcement member is defined at least in part by a perimeter of the gas pressure bladder. In some embodiments, the size and shape of the reinforcement member is defined at least in part by one or more interior attachment features disposed within the gas pressure bladder.

The therapeutic wrap and method of the present invention have other features and advantages which will be apparent from or are set forth in more detail in the accompanying drawings, which are incorporated in and form a part of this specification, and the following Detailed Description of the Invention, which together serve to explain the principles of the present invention.

BRIEF DESCRIPTION OF THE DRAWINGS

FIGS. 10A, 10B, and 10C illustrate a method of assembling a therapeutic wrap similar to that of FIG. 9 in accordance with the invention.

DETAILED DESCRIPTION

Figure 1:
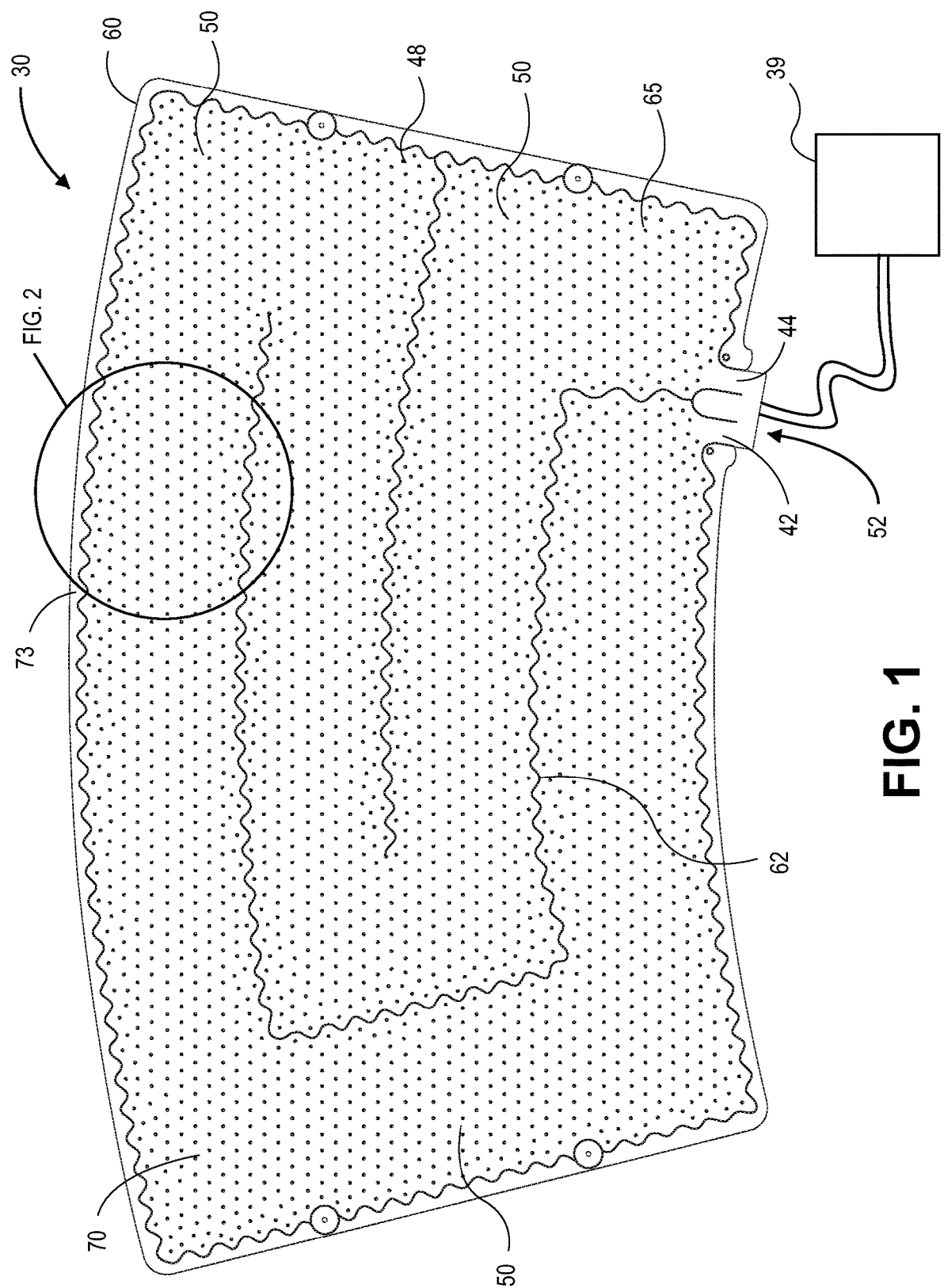
FIG. 1 is a top plan view of a reinforced therapeutic wrap for a straight knee in accordance with the invention, the wrap configured to reduce kinking during operation.

Before the present invention is described, it is to be understood that this invention is not intended to be limited to particular embodiments or examples described, and as such may vary.

For convenience in explanation and accurate definition in the appended claims, the terms "up" or "upper", "down" or "lower", "inside" and "outside", and "interior" and "peripheral" have been used to describe features of the present invention with reference to the positions of such features as displayed in the figures. Unless expressly noted otherwise, the terms used herein are to be understood as broadly used in the art.

In many respects the modifications of the various figures resemble those of preceding modifications and the same reference numerals followed by apostrophes or subscripts "a", "b", "c", and "d" designate corresponding parts.

Turning to FIG. 1, a therapy wrap 30 for use in a therapy system is shown in accordance with the invention. In various respects, wrap 30 is similar to conventional wraps such as those disclosed by U.S. Pat. No. 7,198,093 and U.S. Patent Pub. No. 2005/0256556, the entire contents of which are incorporated herein for all purposes.

As used herein, "wrap" is to be understood as generally used in the art of temperature-controlled therapy and broadly refers to a device including a heat exchanger alone or in combination with a various components for fastening the heat exchanger to a treatment area. In various respects, "wrap" refers to a device including a heat exchanger for containing a heat exchange medium alone or with a sleeve cover. In various respects, "wrap" refers to the sleeve cover, fluid bladder, and compressive element.

Various aspects of the invention are similar to the subject matter described in U.S. patent application Ser. No. 09/127, 256 (filed Jul. 31, 1998) entitled, "Compliant Heat Exchange Panel" issued Apr. 3, 2007 as U.S. Pat. No. 7,198,093; U.S. patent application Ser. No. 09/798,261 (filed Mar. 1, 2001) entitled, "Shoulder Conformal Therapy Component of an Animate Body Heat Exchanger"; U.S. patent application Ser. No. 12/910,743 (filed on Oct. 22, 2010), entitled, "Therapeutic Wrap"; U.S. patent application Ser. No. 09/901,963 (filed Jul. 10, 2001) entitled, "Compliant Heat Exchange Splint and Control Unit"; U.S. patent application Ser. No. 09/771,123 (filed Jan. 26, 2001) entitled, "Wrist/Hand Conformal Therapy Component of an Animate Body Heat Exchanger"; U.S. patent application Ser. No. 09/771,124 (filed Jan. 26, 2001) entitled, "Foot/Ankle Conformal Therapy Component of an Animate Body Heat Exchanger"; U.S. patent application Ser. No. 09/771,125 (filed Jan. 26, 2001) entitled, "Conformal Therapy Component of an Animate Body Heat Exchanger having Adjustable Length Tongue"; U.S. patent application Ser. No. 10/784,489 (filed Feb. 23, 2004) entitled, "Therapy Component of an Animate Body Heat Exchanger" which is a continuation of U.S. patent application Ser. No. 09/765,082 (filed Jan. 16, 2001) entitled, "Therapy Component of an Animate Body Heat Exchanger and Method of Manufacturing such a Component" issued Feb. 24, 2004 as U.S. Pat. No. 6,695,872 which is a continuation-in-part of U.S. patent application Ser. No. 09/493,746 (filed Jan. 28, 2000) entitled, "Cap And Vest Garment Components Of An Animate Body Heat Exchanger" issued Jan. 30, 2001 as U.S. Pat. No. 6,178,562; U.S. patent application Ser. No. 10/122,469 (filed Apr. 12, 2002) entitled, "Make-Break Connector For Heat Exchanger" issued Mar. 29, 2005 as U.S. Pat. No. 6,871,878; U.S. patent application Ser. No. 10/637,719 (filed Aug. 8, 2003) entitled, "Apparel Including a Heat Exchanger" issued Sep. 19, 2006 as U.S. Pat. No. 7,107,629; U.S. patent application Ser. No. 12/208,240 (filed Sep. 10, 2008) entitled, "Modular Apparatus for Therapy of an Animate Body" which is a divisional of U.S. patent application Ser. No. 10/848,097 (filed May 17, 2004) entitled, "Modular Apparatus for Therapy of an Animate Body"; U.S. patent application Ser. No. 11/707,419 (filed Feb. 13, 2007) entitled, "Flexible Joint Wrap"; U.S. patent application Ser. No. 11/854,352 (filed Sep. 12, 2007) entitled, "Make-Break Connector Assembly with Opposing Latches"; and U.S. patent application Ser. No. 10/848,097 (filed May 17, 2004) entitled "Modular Apparatus for Therapy of An Animate Body", published Nov. 17, 2005 as Publication No. 2005/0256556, the entire contents of which patents and publications are incorporated herein for all purposes by reference.

The above-described applications and patents generally describe thermal therapy devices, typically for cooling or heating a body part. In various embodiments, the device and methods of the invention are configured to apply therapy to a mammalian body, and preferably a human body. The wrap may be used on a knee, an elbow, a shoulder, a leg, a hoof, an arm, and more.

Most of the above applications and patents describe an animate body therapy wrap having two major components: a compliant therapy component (e.g., a liquid bladder) covering a body part to be subjected to heat exchange and a control component for producing a flowing heat exchange liquid. Many therapy systems utilize control units that produce and supply air or other gas pressure needed to apply pressure to a body part and to press the therapy component toward a body part. This gas pressure is contained in a compliant bladder such as a gas pressure bladder. The gas pressure bladder overlays the liquid bladder to press the liquid bladder against the body part to be subjected to heat exchange, as well as apply compression to the body part to reduce edema. In general, the compliant liquid bladder contains a circulating heat exchange liquid and the gas pressure bladder overlays the liquid bladder for pressing the liquid bladder against the body part.

Figure 5:
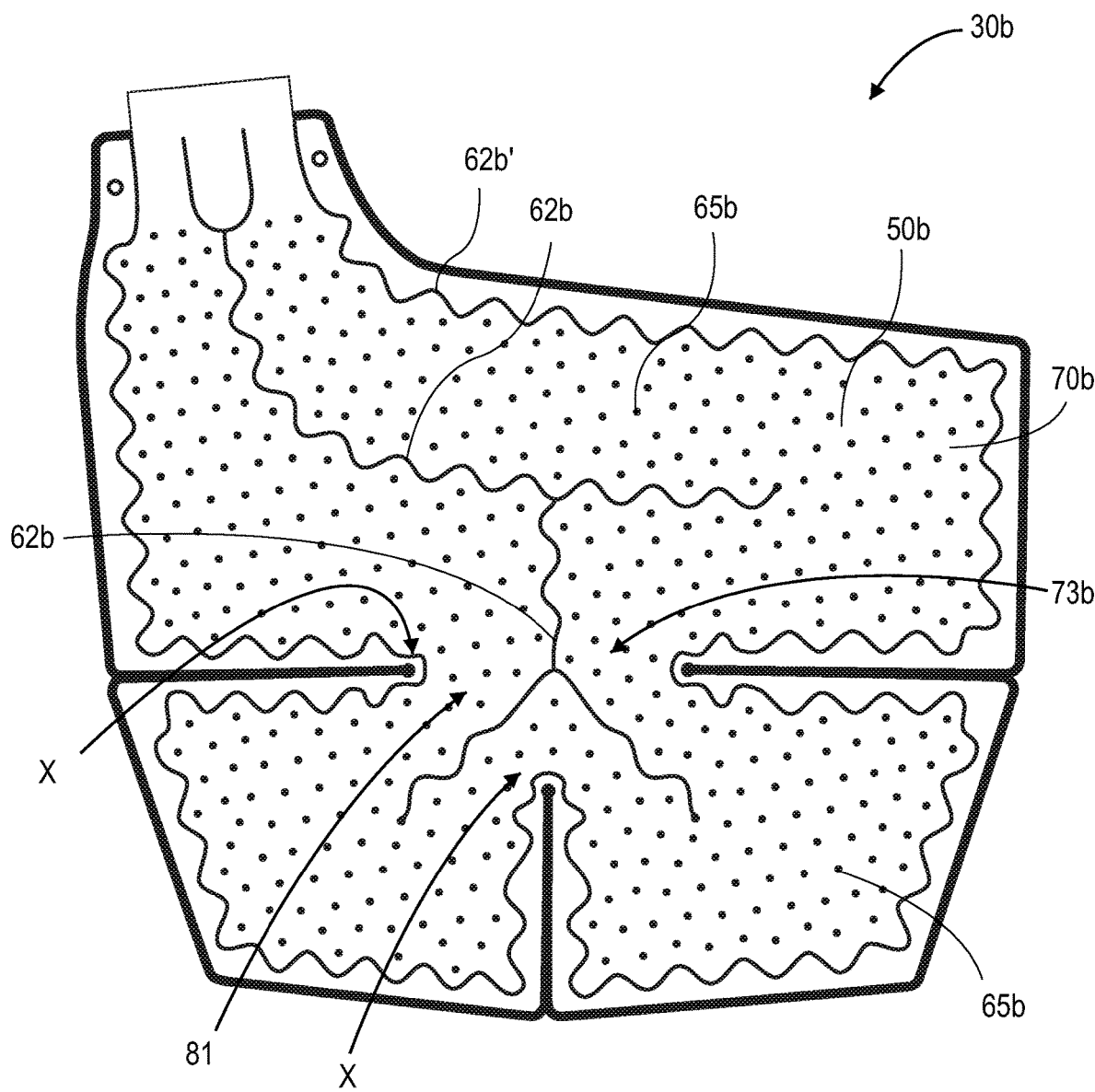
FIG. 5 is a top plan view of another selectively reinforced therapeutic wrap similar to the wrap of FIG. 1, the wrap configured for a canine.
Figure 6:
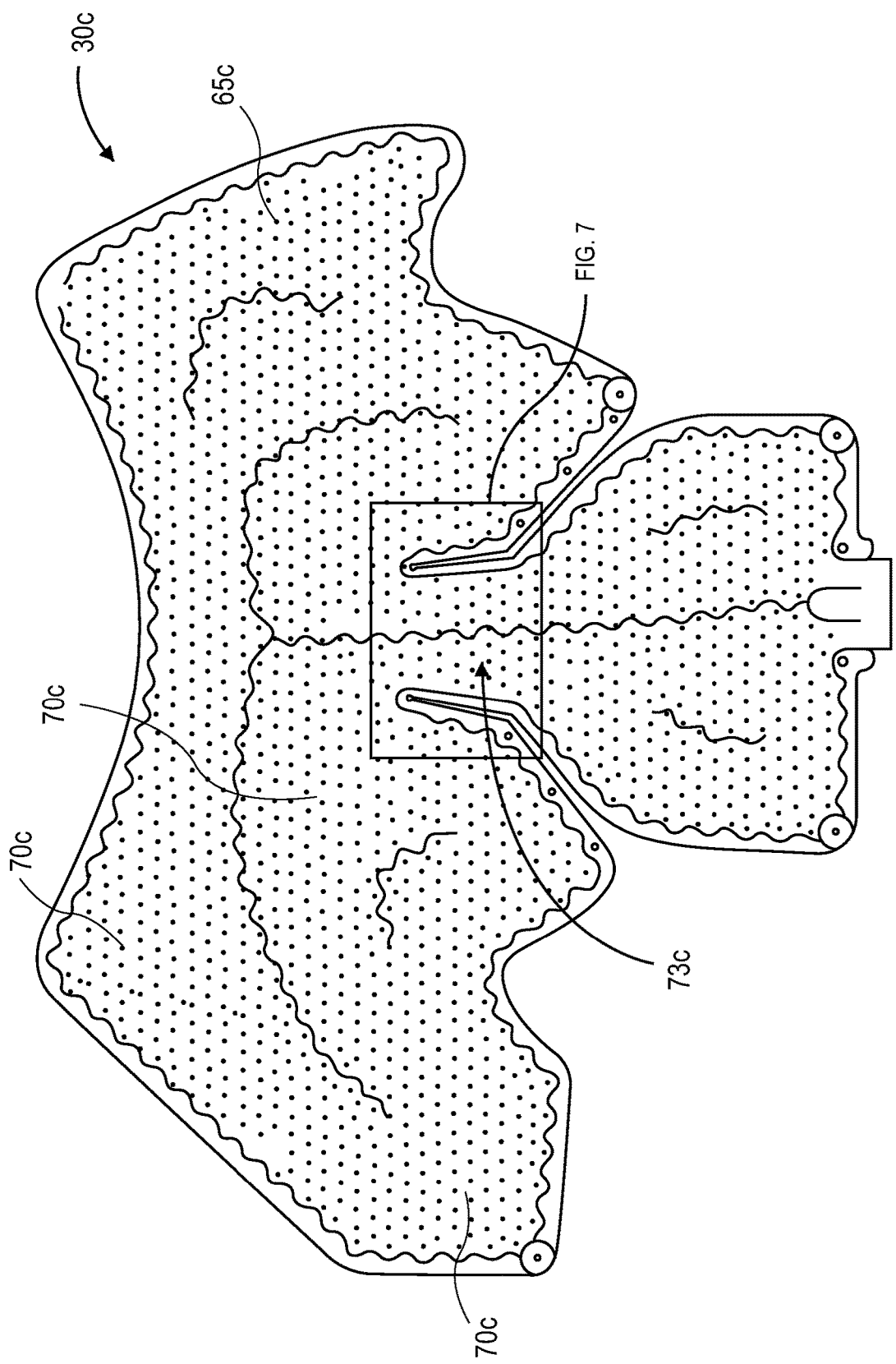
FIG. 6 is a top plan view of another selectively reinforced therapeutic wrap similar to the wrap of FIGS. 1 and 5, the wrap configured for a human shoulder.

Turning to FIGS. 1, 5, and 6, several therapy wraps 30, 30a, and 30b are shown. Wrap 30 of FIG. 1 is a circumferential wrap for applying to a body part such as a knee, an elbow, an arm, or a leg of a human body. Wrap 30b of FIG. 5 has a shape for applying to a canine. Wrap 30c of FIG. 6 has a shape for applying to a shoulder of a human body. In many respects, elements of wraps 30, 30a, and 30b are functionally and structurally similar and thus will be described together.

With reference to FIGS. 1, 2, 3, and 4, therapy wrap 30 is configured to provide temperature-controlled therapy to an anatomical body part. The wrap includes a pair of layers 33, 35 defining a flexible fluid bladder 37 through which a heated or cooled liquid is circulated. The liquid fed to the wrap is maintained at a desired inlet temperature. Generally, the desired temperature is lower than the temperature expected for the body part to effectuate heat exchange. Cooling or heating of the fluid is typically achieved, at least in part, by passing the liquid through the heat exchanging medium before providing the fluid to bladder 37. For example, the liquid can be passed through an ice bath or a refrigeration unit. In various embodiments, the system includes a pump and control unit, generally designated 39, for controlling one or more of the temperature of the fluid supplied to the inlet of the fluid bladder, fluid flow rate, and fluid flow pressure. One such system is disclosed, for example, in U.S. Pat. No. 6,178,562, the entire content of which is herein incorporated for all purposes by reference.

Performance of the thermal therapy device may be improved by adjusting the flow rate, adjusting the temperature, and/or providing additional features to the thermal therapy device. In a typical return flow arrangement, the velocity of the fluid is proportional to the flow rate into the wrap. Keeping the inlet temperature the same, reducing the flow rate through the thermal therapy device will reduce the amount of energy removed from (or added to) the body part requiring treatment. Conversely, increasing the flow rate will increase the amount of energy removed from (or added to) a patient. In a cold therapy device, with the wrap applied to a mammalian body, the temperature of the fluid leaving the wrap is warmer than the temperature of the fluid entering the wrap because the mammalian body is typically warmer than the thermal fluid.

As the fluid flow rate into the wrap becomes slower, the temperature delta increases as does the average wrap temperature. To decrease the average wrap temperature, the flow may be increased. A slower flow rate, however, may lead to less efficient heat transfer and other performance problems. Conversely, a blockage in the fluid bladder that reduces the flow rate negatively affects performance. Similarly, blockages in the flow lead to slowed or stagnant flow and "cold spots" where heat transfer is uneven, ineffective, or nonexistent. In other cases, blockages can lead to cold spots or hot spots.

As used herein, the "average temperature" of the wrap refers to the average of the wrap inlet temperature and the wrap outlet temperature. The difference between the wrap outlet temperature and the wrap inlet temperature will be referred to as "temperature delta" through the wrap. The temperature delta through the wrap depends on the fluid flow rate, the heat load, and the specific heat of the thermal fluid. The "maximum temperature" and "minimum temperature" refers to the maximum and minimum temperatures at any point in the wrap, and more specifically the fluidic channels. In general, it is desirable to provide turbulent yet uniform flow and consistent heat transfer whereby the temperature increase between the inlet temperature and outlet temperature is linear, in the case of a cold wrap.

The exemplary device 30 illustrated in FIG. 1 is a modular heat therapy device or "wrap." The wrap includes a first modular member or portion and one or more other modular members. The first modular member or portion comprises a heat exchanger. In the illustrated embodiment, the heat exchanger is fluid bladder 37 for circulating a heat exchange medium such as ice water. In the illustrated embodiment, the second modular member comprises a gas pressure bladder 38 for applying a compressive force against the fluid bladder and treatment site.

In various embodiments, the wrap includes another modular member, sleeve 41, which acts as a cover for the bladder(s). The exemplary sleeve forms a pouch into which the heat transfer device and gas pressure bladder are placed. The sleeve is adapted to be wrapped around at least a portion of a patient's body requiring treatment.

Various aspects of sleeve 41 are similar to those disclosed in U.S. Patent Pub. No. 2005/0256556 to Schirrmacher et al. and U.S. Pat. No. 6,695,872 to Elkins, the entire contents of which are incorporated herein for all purposes by reference. The sleeve may comprise an inner or front side portion and an outer or back side portion. The sleeve may be formed of various materials understood in the art and may comprise inner and outer sheets of material that are sewn or fused together. For example, the inner and outer sides can comprise two sheets of fabric that are sewn together to form a seam. An additional interior seam may be provided to form a flap which is adapted to receive one or more of the wrap components. Suitable materials for the sleeve include, but are not limited to, nylon, spun bonded material, hook and loop material, and more.

Figure 4:
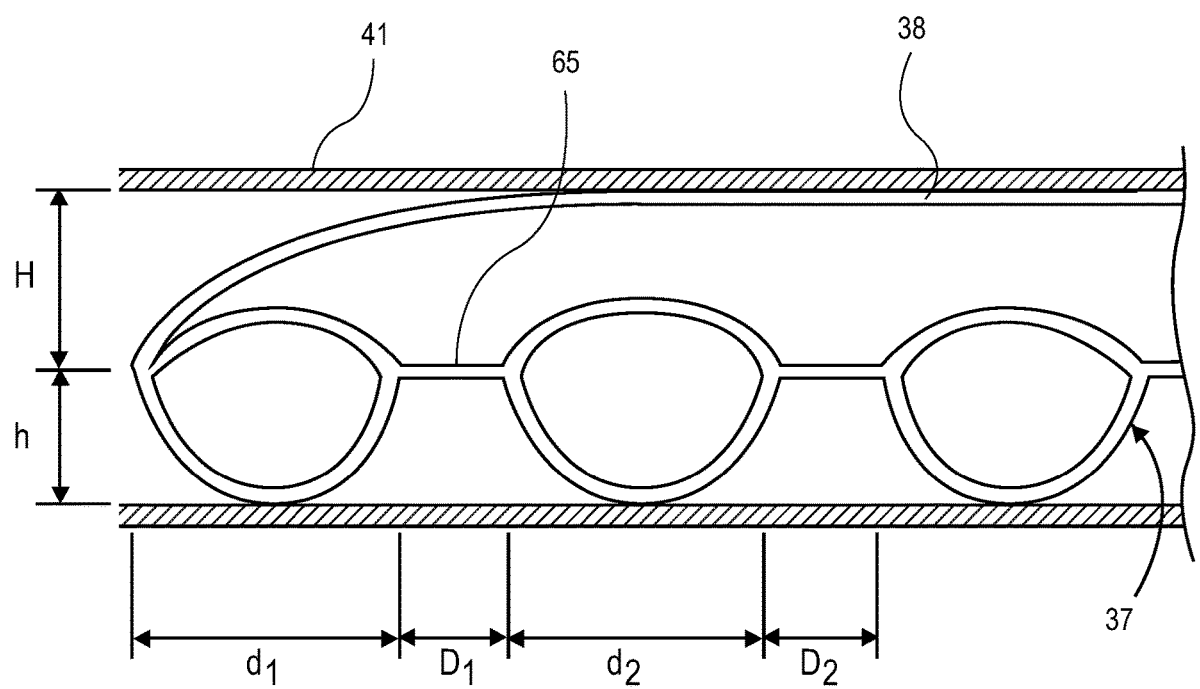
FIG. 4 is a schematic drawing representative of an enlarged portion of the wrap of FIG. 3, illustrating a plurality of fluidic channels expanded with fluid.

In the exemplary embodiment of FIG. 4, fluid bladder 37 and gas pressure bladder 38 are contained within sleeve 41. The illustrated sleeve is composed of nylon on one side and a loop material (e.g., pile) on an opposite side. The exemplary sleeve also includes a fastener for holding the wrap device in the desired location on the animate body. Accordingly, when the device is wrapped around a portion of or the entire region being treated, the fastener holds the device in place during treatment. In the illustrative embodiment, a hook and loop fastener is used. If the hook and loop fastener wears out, the removable modular bladder or sleeve can be readily replaced.

Figure 8:
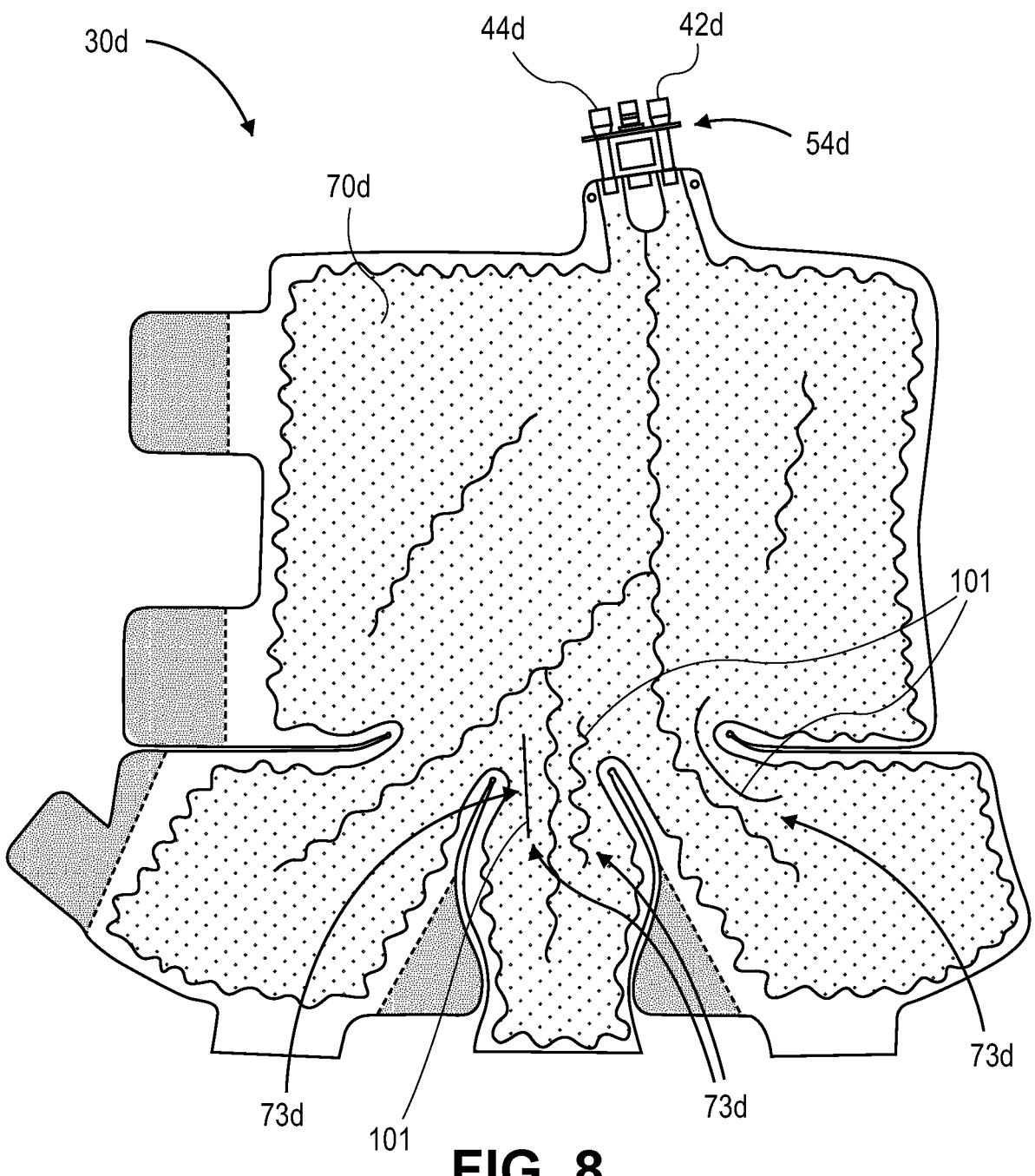
FIG. 8 is a top plan view of a therapeutic wrap for a horse hoof in accordance with the invention, illustrating various kink-resistant zones with different reinforcement member positions and configurations.

In various embodiments, the hook material portion of the hook and loop fastener comprises two sections (shown in FIG. 8). In the illustrated embodiment, each section has a length extending along the length of the strap of about 4 or 5 inches. These sections can be spaced apart by about 1 inch to facilitate or improve flexibility of the end portion of the strap. In this manner, the strap can be readily folded to provide length adjustment for differently sized users. In the illustrative embodiment, the active areas of the hook portion of the hook and loop fastener are outside the seams forming the pouch, which can alleviate excessive force when the wrap is under compression.

Figure 3:
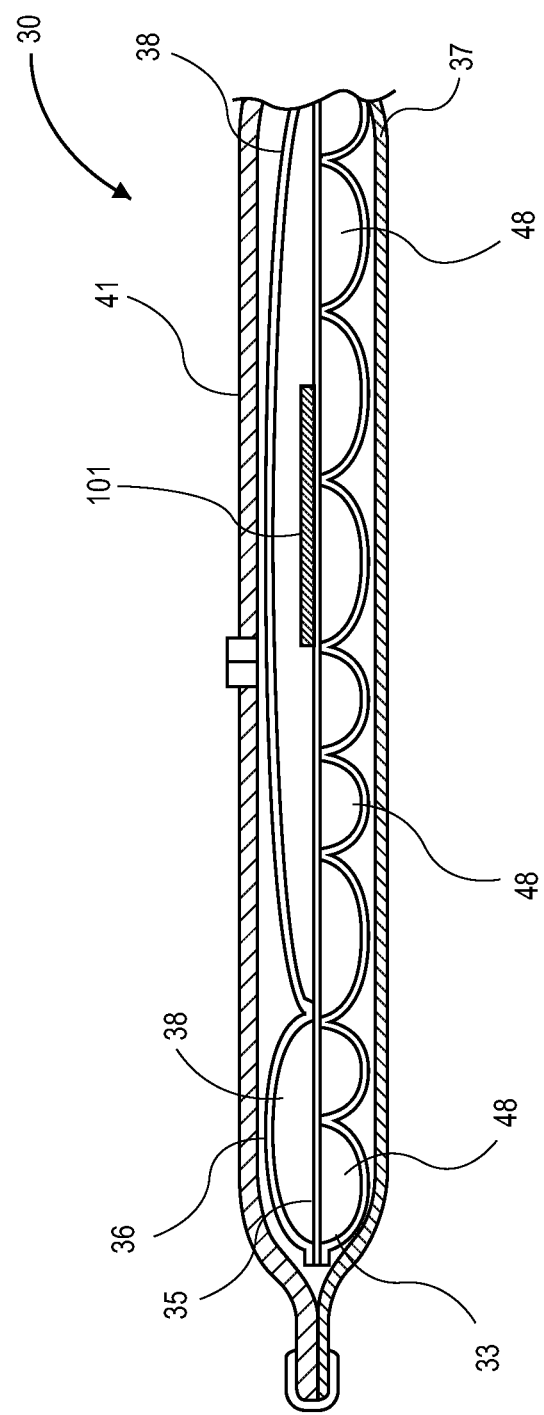
FIG. 3 illustrates a sectional view of the wrap of FIG. 2 through the line 3-3, illustrating the expandable compression bladder and fluid bladder within a sleeve along with an optional reinforcement member.

Referring to FIGS. 3 and 4, the modular bladders are positioned inside sleeve 41 in a sandwich configuration. In this state, the apparatus is ready to apply to the portion of the body to be treated. In various embodiments, the exemplary pouch formed by the sleeve allows fluid bladder 37 and gas pressure bladder 38 to move freely inside. In other words, beyond being confined in the pouch, there are no connections between fluid bladder and gas pressure bladder. In various embodiments, the fluid bladder and gas pressure bladder are not attached to each other or the sleeve but are fit tightly in the sleeve to reduce any relative movement. The sleeve pouch thus locates the two components relative to each other. This can provide a more evenly distributed compression around the gas bladder, resulting in improved therapy of the body being treated. In various embodiments, the fluid bladder has some room for movement within the pouch such that there is less chance that a portion of the fluid flow is blocked when the wrap is improperly applied to the portion of the body being treated. For example, if an unexpected fold occurs, the fluid bladder may self-correct its position and relieve blockage of coolant flow. In various embodiments, other components may be positioned and located within the sleeve in similar manner and as would be understood by one of skill in the art from the description herein. In the exemplary embodiment, the fluid and gas pressure bladders are integrally formed and positioned snugly within a sleeve.

The exemplary modular members—fluid bladder 37 and gas pressure bladder 38—can be readily removed from sleeve 41 so that one can clean either or both and/or replace either component. The bladders and/or sleeve can be constructed of a washable or reusable material. This may be helpful in applications where the elements may need to be cleaned after being stained with blood or otherwise soiled. In various embodiments, one or both of fluid bladder 37 and gas pressure bladder 38 are compliant and formed of flexible material.

As used herein, "flexible" is to be understood as generally used in the art. In various respects in connection with the materials and structures described herein, "flexible" refers to tensile bending strength (i.e. can bend transversely) whereas "expandable" refers to stretching. In various respects, "flexible bladder" refers to a bladder that can be bent and applied to curves and contours of a body part during use.

Exemplary fluid bladder 37 includes an inlet 42, outlet 44, and at least one fluidic channel 48 connecting the inlet and outlet. The first layer 33 and middle layer 35 are joined together along a common border to form the fluid bladder. As will be described below, a series of fences, walls, and other features define a fluid flowpath 50 between the first and middle layers. "Treatment surface" and "treatment area" are to be understood as broadly used in the art. In the exemplary case, the treatment surface generally refers to the surface in contact with the heat exchanger and the body part requiring treatment. This surface is generally bounded by the border and periphery of the fluid flowpath.

As used herein, "fluid flowpath" or "fluid pathway" refers to a general path of the fluid flow between the inlet and outlet. In a width direction, the flowpath is defined by adjacent features selected from one of a wall of the bladder, a fence, a weld line, and a combination of the same. "Fluidic channel" refers to a channel within a flowpath formed between adjacent attachment points or other features.

Figure 7:
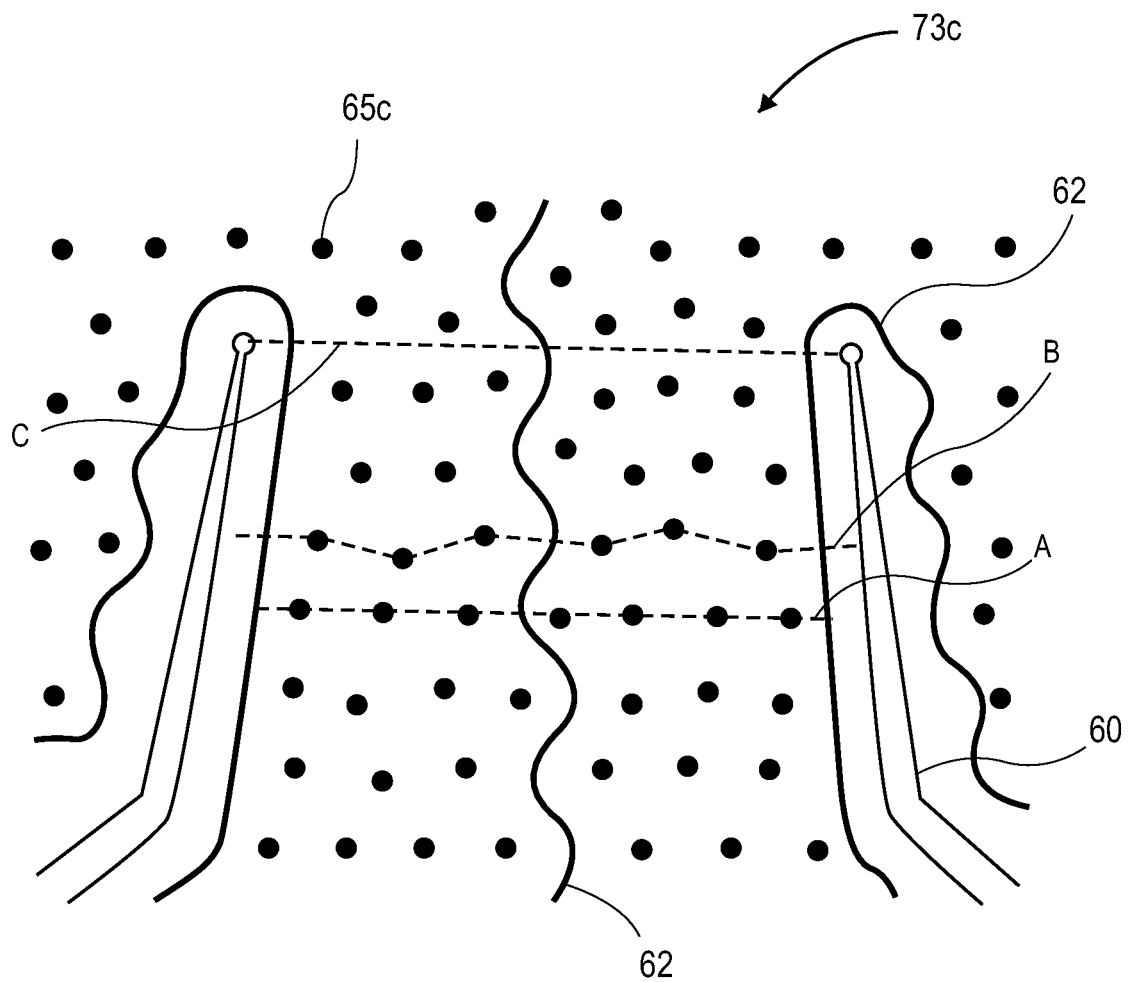
FIG. 7 is an enlarged detail view of the wrap of FIG. 6, illustrating variable dot patterns in a narrow connecting region between flaps.

Referring to FIG. 7 for illustrative purposes, a flowpath 50 is defined by a peripheral fence 62 adjacent a wall 60 and an interior fence 62 within the fluid bladder. In turn, flowpath 50 is divided into a plurality of fluidic channels 48 by a series of attachment points. The attachment points connect opposite walls of the bladder in a thickness direction (shown, e.g., in FIG. 3).

The exemplary attachment points, generally designated 65, are formed by spot welding. In various respects, the attachment points are referred to informally as "dots." The dots may be performed with conventional techniques such as RF or heat welding. The exemplary dots are circular based on the nature of the welding process, but one will appreciate that the dots may have different shapes.

"Attachment point" is to be understood as used in the art and generally refers to points that are essentially one-dimensional as opposed to lines, shapes, and other similar features. The dots are similar in many respects to fences except that they are single points rather than a shape or line.

In some respects, "fluidic channel" may refer to the entire flowpath from wall-to-wall in a width direction or any sub-unit within the flowpath depending in part on the use and position of fences and dots.

In various embodiments, the fluid bladder and gas pressure bladder are integrally formed. In various embodiments, fluid bladder 37 and gas pressure bladder 38 form separate chambers positioned adjacent each other. In various embodiments, the chambers are generally parallel to one another and are made so as to preclude fluid communication between the two during use.

Exemplary gas pressure bladder 38 is formed by joining middle layer 35 to a second layer 36 on an opposite side of the middle layer from first layer 33. Thus, exemplary bladders 37 and 38 are formed from three sheets of material joined along a common border (e.g., wall 60). The gas pressure bladder includes a single port 52 for regulating gas in and out of the bladder.

In an exemplary embodiment, all layers 33, 35, and 36 are formed of polyurethane with nylon. Suitable materials for the fluid bladder and gas pressure bladder include, but are not limited to urethane, polyvinyl chloride (PVC), polyurethane (PU), nylon, and more. In various embodiments, the fluid bladder and gas pressure bladder are made of a flexible plastic.

Referring to FIGS. 1-4, inlet 42, outlet 44, and port 52 are housed within or connected to a single, quick-connect plug or manifold 54. Each exemplary port is formed by a tubular member, which has one end adapted to receive a hose connector and another end adapted to be inserted into one of three tubes extending from the bladder as is known in the art. The hose connector connects the bladders to a hose that in turn connects to pump and control unit 39.

In various embodiments, one or more of the manifold fluid inlet 42 and outlet 44 includes a valve configured to allow the passage of fluid therethrough when the fluid hose connectors are coupled to the manifold and to prevent fluid flow therethrough when the fluid hose connectors are uncoupled. Suitable valves known in the art may be used such as a poppet or check valve. The exemplary inlet and outlet include a spring-loaded poppet valve. In this manner, fluid such as a liquid coolant is blocked from exiting fluid bladder 37 when the fluid hoses are uncoupled from the manifold. The exemplary gas port does not include a valve.

In various embodiments, fluid bladder 37 is adapted to receive and circulate a fluid, such as a coolant, which can be in the form of a cold liquid, to transfer heat away from the animate body part. Alternatively, the fluid supplied to fluid bladder can have a temperature higher than the body so as to heat the animate body part.

Gas pressure bladder 38 is adapted to receive a gas (e.g., air), which can be regulated to provide the desired amount of inflation of the bladder or pressure therein. This inflation or pressure affects the compressive force applied to the fluid body, and consequently the animate body, during use. Specifically, the gas pressure bladder overlays the fluid bladder as illustrated in FIG. 4 such that the gas pressure bladder directs gas pressure against the fluid bladder to press it towards the portion of the body being treated. In various embodiments, the gas pressure bladder is inflated to a pressure between 0 psig and about 5 psig, preferably between about 0.2 psig and about 3 psig, and more preferably between about 0.25 psig and about 1.5 psig. In various embodiments, the gas pressure bladder is inflated to a pressure above 5 psig. In general, the gas pressure bladder is enclosed between sleeve 41 and fluid bladder 37. Thus, the pressure of the gas pressure bladder is directed to the fluid bladder, which in turn compresses the body part.

One will also appreciate that the compressive gas pressure is also based on the middle layer which forms a common wall with the fluid bladder and gas pressure bladder. In other words, the middle layer may be configured to adjust the compressive force. As will be apparent from FIG. 4, for example, a more rigid middle material may adjust the balance between the pressure in the expanded fluidic channels and gas pressure bladder. The shape of the fluidic channels will also change. In various embodiments, the flexible material forming the middle layer is selected based on the desired compressive pressure.

In various embodiments, the gas pressure bladder is at a lower pressure than the fluid bladder. In an exemplary embodiment, sleeve 41 holds wrap 30 taut against the body part requiring treatment. Accordingly, as pressure is applied to gas pressure bladder 38, it has little room to move and the pressure is directed primarily against the fluid bladder. Thus, even low pressures in the gas pressure bladder accumulate pressure on the fluid bladder.

One will appreciate from the description herein that the material type and content may be modified based on the intended operational parameters and desired filling of the fluid bladder and gas pressure bladder. Moreover, one will appreciate that material selection and the configuration of the middle layer may be modified depending on the desired interaction between the gas pressure bladder and fluid bladder. For example, a stiffer middle layer may be used to distribute pressure from the gas pressure bladder to the fluid bladder more uniformly. The middle layer and outer second layer also may be selected and configured to control the amount of "ballooning" of the gas pressure bladder on each side.

Exemplary wrap 30 includes a plurality of fences 62 and dot connections 65. More specifically, and with particular reference to FIGS. 2, 3, and 4, a plurality of connections between walls 60 defining fluid bladder 37 or gas pressure bladder 38 can be provided. The connections and their method of manufacture are similar in some respects to those disclosed by U.S. Pat. No. 6,695,872 to Elkins and U.S. Pat. No. 4,149,541 to Gammons et al., the entire contents of which patents are hereby incorporated herein for all purposes by reference. Such connections can minimize or eliminate undesirable ballooning when the fluid and/or gas pressure bladder is pressurized. In the illustrative embodiment, in which the bladders are formed by RF welding (see, e.g., FIGS. 10A, 10B, and 10C), reduction of ballooning is achieved by forming some of the interior connections in the fluid bladder while the materials 33 and 35 are in place as will be described in more detail below. Other connections, such as the peripheral border and fence, are formed while the materials 36 and 35 are in place. The result is that many of the connections extend through the fluid bladder and gas pressure bladder.

The shape of exemplary gas pressure bladder 38 conforms to the shape of exemplary fluid bladder 37. Fences or dividers 62 in the fluid bladder are configured to direct fluid flow in the fluid bladder and can also be provided in the gas pressure bladder. These control fences can be provided not only for the purpose of directing the flow of a liquid or gas but also to secure the walls defining the bladder together at various locations within the interior of such bladder. As described above, these connections can prevent the bladder from "ballooning" thereby preventing the wrap from conforming to the body part. In the illustrated embodiment, most or all of the fences in the gas pressure bladder register with the comparable fences in the fluid bladder.

Although adding connections provides the above benefits, an excessively large number of connections can increase the risk of kinking. As the welds takes up a larger percentage of the treatment surface, the material becomes stiffer. At a certain level, the bladder becomes so stiff as to be difficult to conform to a body part. As discussed above, a greater number of connections also reduces the amount of shearing and movement between the material layers. Accordingly, various aspects of the invention are directed to the careful configuration of dot spacing, size, and shape to provide a wrap with good fluid circulation while reducing the risk of kinking.

With continued reference to FIGS. 1, 2, 3, and 4, wrap 30 includes a reinforced portion to increase the wrap's kink resistance in accordance with various aspects of the invention. In various embodiments, the wrap includes selective reinforcement. In various respects, "selectively reinforced" generally refers to providing reinforcement in specific, targeted locations relative to the remainder of the wrap. In various respects, "selectively reinforced" generally refers to providing a variable amount of reinforcement along the wrap surface. "Reinforcement" and "reinforced" are to be understood as generally used in the art and may refer to modifications and configurations of existing elements and/or the addition of distinct members to provide reinforcement and/or increase strength. As will be described below, the reinforcement may be provided in the way of external structural members with increased structural rigidity or a different configuration of the same materials to resist kinking and/or bending.

A technique for selective reinforcement of the wrap by adjusting the dot connections will be described with reference generally to FIGS. 1-7. A wrap in accordance with the invention may include a selective reinforcement region corresponding to a kink-prone region. As used herein, "kink-prone region" generally refers to a region presenting conditions conducive to kinking absent the techniques described herein. "Kink-resistant zone" and "reinforcement region" generally refer to a zone or local region of the device configured to counteract such conditions. In various respects, "kink-prone region" and "kink-resistant zone" are used interchangeably. Functionally, kink resistance may be expressed in terms of increased tensile or bending strength, or a decreased minimum bend radius.

As illustrated, for example, by the wrap in FIG. 1, the kink-prone region may correspond to the body part to which the wrap is applied. The wrap shown in FIG. 1 is a circumferential wrap which may be applied to an anatomical joint such an elbow or knee. With a conventional wrap configuration, the fluid bladder risks bunching and forming "wrinkles" with tight radiuses when the joint is flexed.

Along the back of the knee, conventional wraps tend to collapse because the void formed by the back of the knee removes any support of the fluid bladder against the compressive air bladder. The exemplary wrap of FIG. 1 incorporates several of the features described herein to overcome these and other drawbacks of conventional wraps.

Exemplary wrap 30 includes a reinforcement region having a plurality of fences and dots in a special configuration to increase resistance to bending or kinking. A portion of the interior of the fluid bladder 37 away from kinking features include a relatively uniform distribution of dot connections 65, referred to in some respects as an "open area" or "open field" and generally designated 70. In some respects, "open area" or "open field" are to be understood as generally used in the art and refers to a portion of the flowpath away from a region that is subjected to folding. In various respects, "open area" refers to a portion of the wrap that does not undergo bending near or beyond a kink radius of the bladder during normal use. The exemplary bladder also includes a selectively reinforced pattern of dot connections configured to resist kinking in other portions of the bladder referred to as kink-resistant zones, generally designated 73.

A traditional method for reducing the likelihood of kinking is to make the entire bladder more rigid (e.g., assembling from more rigid materials) or avoid bending of the structure beyond the kink radius, also referred to as the minimum bend radius. By contrast, the internal structure of the selectively reinforced fluid bladder of FIG. 1 is modified to decrease the kink radius in the bending region, strengthen the material to limit the local amount of bending, or both. In various embodiments, the kink radius of the local kink-resistant zone is about 5 mm or less. In various embodiments, the entire wrap has a kink radius of about 5 mm or less. In various embodiments, the kink radius of the kink-resistant zone is at least 10% smaller than the kink radius of any other remaining portion of the wrap, and more preferably at least 25%, at least 50%, or at least 75% smaller.

As shown in FIG. 7, a series of adjacent dots 65 form an imaginary line. Dots in alignment form a straight line as denoted by line "A" in FIG. 7. On the contrary, dots in an irregular or random pattern form a crooked, non-linear line, at best. In the exemplary wraps of FIGS. 1-7, dots in an open area have a regular pattern that form crossing imaginary lines as described, for example, in U.S. Pat. No. 6,695,872, incorporated herein for all purposes by reference. In the kink-resistant zones, however, the dots are positioned to avoid forming a straight line as denoted by line "B" in FIG. 7.

It has been found that some kinking tends to occur near an apex or corner of flaps of the fluid bladder (represented, e.g., as "X" in FIG. 5). In various embodiments, the dots are aligned to direct bending stress away from high stress areas. In various embodiments, the dots are aligned to limit stress concentrations in the kink-resistant zone. As the flap is folded, the material wants to form along a so-called "hinge line" between the weakest points, in the exemplary case, two corners depicted by line "C" in FIG. 7. Accordingly, the selectively reinforced dot pattern may be positioned to form a line of weakness to direct bending stress away from the apexes and into an open field where the material has more room to bunch up.

In various embodiments, the dots in a kink-resistant zone are aligned in a pattern to form an imaginary line orthogonal to a local fence or wall. In various embodiments, the dots are positioned to control bending along a line at an obtuse angle to the fluid flow. In various embodiments, the dots in a kink-resistant zone are positioned without any linear arrangement. In other words, the dots form an imaginary line that is non-linear. As shown, for example, in FIG. 7, non-linear line "B" is crooked and does not extend in any single direction.

In various embodiments, the selectively reinforced dot pattern is aligned over a fluidic channel and/or fluid flowpath. In various embodiments, the selectively reinforced dot pattern is positioned entirely within a fluid flowpath. In various embodiments, the selectively reinforced dot pattern overlaps two or more fluid flowpaths.

Figure 2:
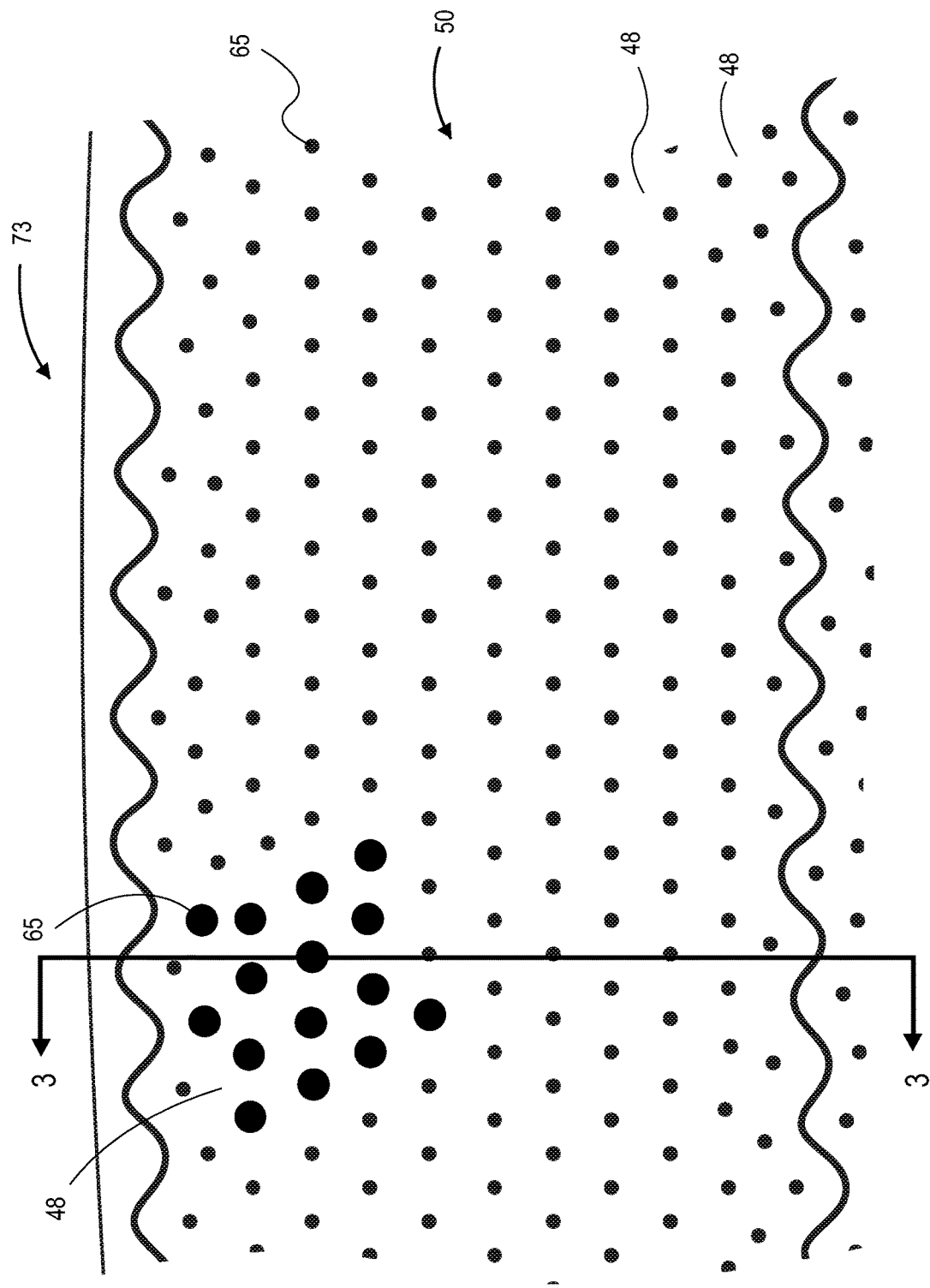
FIG. 2 is an enlarged detail view of the wrap of FIG. 1, illustrating a variable dot pattern in a kink-resistant zone of the fluid bladder.

Referring to FIGS. 2 and 7, dots 65 may have various positions and configurations. In various embodiments, the dots have different diameters. In various embodiments, the average dot diameter is larger in a local region of bending than in open areas. In various embodiments, the dot diameter is variable. As shown in FIG. 2, the dot diameter may generally decrease moving in a direction away from a local fence or wall and towards an interior of the bladder. In various embodiments, the dot diameter generally decreases moving in a direction from a fluid pathway wall towards a middle of the pathway. In various embodiments, the local spacing between dots is proportional to the diameter of the dots. In various embodiments, the spacing between the dots generally increases as the diameter of the dots decreases. These and other configurations may further act to preferentially reduce stress concentrations and increase kink resistance.

Reiterating the description above and with reference to FIGS. 1-4, exemplary fluid flowpath 50 is defined by a space between first outer layer 33 and middle layer 35 on a top and bottom and walls 60 and fences 62 on each side. Within the flowpath, attachment points (dots) 65 further define a plurality of fluidic channels 48. As shown in FIG. 4, the fluidic channel is surrounded by materials 33 and 35. The attachment points pinch shut the bladder to form the fluidic channel. As shown in FIGS. 3 and 4, the width of the fluid pathway thus comprises alternating fluidic channels and weld spots. Accordingly, the fluidic channel dimension is based on the location of the dots. The dimensions are also a function, to an extent, of the elasticity of the materials 33 and 35 and pressure in the respective channel. In various embodiments, the second outer layer 36 and middle layer 35 are formed of a material that is relatively resistant to stretching, for example, on the order of millimeters of stretching over the entire length of the wrap.

Conventionally, dots were added to bladders and expandable fluid chambers to reduce the effects of "ballooning." The dots also tended to be distributed across the bladder in a somewhat uniform and proportional manner based on a simple view of cost and manufacturability. For example, previously the dot diameter could be based on tooling costs and overall bladder size. The dot configuration in accordance with the present invention, by contrast, generally reduces the occurrence failure modes while maintaining or improving performance. In various respects, the dot configuration takes into account several performance and operational concerns in addition to manufacturing concerns.

As discussed above, the dot configuration may be important to increasing kink resistance while maintaining effective heat exchange performance. Several considerations are taken into account in selecting the dot spacing, size, and other factors. In general, the various factors must be within a specific range to achieve optimum performance. By example, it is understood that increasing the dot size can provide a stronger weld, but it has been found that increasing the size above a certain level decreases performance because the bladder becomes too rigid. In part, it is believed that the bladder becomes too rigid to conform and compress around the body part. Similarly, decreasing the weld size may reduce kinking at the expense of weld strength. Accordingly, the dot configuration described below involves the careful and complex balancing of many factors.

FIG. 4 is a representative sketch of a typical series of fluidic channels and gas pressure channel in a kink-resistant zone. As shown in FIG. 4, a first fluidic channel has a width "d1" and height "h1" when filled with fluid. A second fluidic channel has a width "d2" and height "h2". The diameter of dots 65 are represented as widths "D1" and "D2" in the figure. Likewise, the cross-sectional area of each fluidic channel is based on d and h. As used herein, "average" refers to an average within a local reference area. For example, an average dot diameter in the exemplary view of FIG. 4 is the average of D1 and D2.

In various embodiments, d1 and d2 are essentially equal. In various embodiments, d1 and d2 are different. In various embodiments, D1 and D2 are essentially equal. In various embodiments, D1 and D2 are different.

In various embodiments, h is variable through the kink-resistant zone, open areas, or both. In various embodiments, H is variable through the kink-resistant zone, open areas, or both. In various embodiments, h is about 0.1 inch, and more preferably 0.175 inch.

In an exemplary embodiment, the dots have an average diameter between about 0.05 inch and about 0.2 inch in open areas. In an exemplary embodiment, the dots have an average diameter of about 0.09 inch in open areas. In various embodiments, the average diameter is larger in a selected kink-resistant zone than in open areas.

In various embodiments, the dots in the kink-resistant zone have a diameter in a range of between about 0.15 inch and about 0.4 inch, preferably between about 0.15 inch and about 0.35 inch, more preferably between about 0.15 inch and about 0.2 inch, and more preferably between about 0.16 inch and about 0.2 inch. In various embodiments, the dots in the kink-resistant zone have an average diameter of about 0.15 inch. By comparison, conventional wraps typically have a smaller or larger dot diameter. One example of a conventional wrap includes a fluid bladder with dots have an average diameter of about 0.5 inch.

The dots may be formed from a conventional tool. In various embodiments, the dots in the kink-resistant zone are formed from a tool die that has a diameter of about 0.093 inch. In various embodiments, the tool die diameter is about 0.09 inch. In various embodiments, the tool die diameter is in the range of between about 0.05 and about 0.25 inch.

In various embodiments, the welding parameters are varied to achieve a dot diameter of between about 0.15 inch to about 0.2 inch. In various embodiments, the dots in the kink-prone region and open areas are formed by the same tool but with different processing conditions. For example, the same tool can be used across the entire wrap but the weld temperature and/or time may be increased in the kink-resistant zone to produce larger dots.

In various embodiments, the dot connections in the kink-resistant zone are positioned and configured to maintain the average fluidic channel cross-sectional area above a predetermined threshold. In various embodiments, the dot connections in the kink-resistant zone are positioned and configured to maintain the cross-sectional area of each of the fluidic channels above a predetermined threshold. In various embodiments, the dot connections in the kink-resistant zone are positioned and configured to maintain the average fluidic channel cross-sectional area below an upper predetermined threshold. In various embodiments, the cross-sectional area of the fluidic channels in the kink-resistant zone is about 0.02 sq.-in, and more preferably 0.0254 sq.-in.

At a certain fluidic channel volume, the performance of the wrap is negatively affected. For example, an excessively large cross-sectional area of the fluidic channels (such as by providing a very high "h" value, "d" value, or both) leads to high fluid volume in the wrap. When the volume is too high, the heat exchange fluid takes undesirably long to circulate through the wrap and becomes difficult to maintain to provide effective therapy even when adjusting the inlet temperature. For example, it has been found that a fluid bladder having a fluid volume of 4000 mL/m$^2$ exhibits poor heat exchange performance compared to the exemplary wrap 30. Also, at such large fluid volumes the wrap loses the ability to conform to a complex shape at higher pressures. In the example above of a bladder with 4000 mL/m$^2$, the pressure typically must be low, in the range of 5 psi to maintain flexibility. At low pressures, however, heat exchange is decreased and the time to circulate fluid through the wrap is increased significantly. By contrast, the exemplary wrap allows for smaller fluidic channels without the risk of buckling of the channels at water volume levels having good operational performance.

In various embodiments, the cross-sectional area of the fluidic channels in the kink-resistant zone is in a range between about 10 mm$^2$ to about 40 mm$^2$, preferably about 15 mm$^2$ to about 25 mm$^2$.

In various embodiments, the distribution of dot connections is varied across the fluid bladder to achieve kink resistance in selected areas. For example, as shown in FIG. 6 described below, the distribution of dots in the kink-resistant zone is lower than in the open areas. In this manner, the fluidic channels have a larger cross-sectional area in the kink-resistant zone to reduce the risk of occlusion and/or increase the restoring force from the fluid in the channel.

It has been found that the total fluid volume relative to the treatment area of the fluid bladder can be important in certain applications. This ratio may be referred to in terms of total volume of the fluid bladder in liters relative to a flat treatment surface area of the bladder in square meters. In various embodiments, this fluid volume/treatment area ratio at about 10 psi is between about 1000 mL/m$^2$ and about 2000 mL/m$^2$, preferably between about 1000 mL/m$^2$ and about 1500 mL/m$^2$, and more preferably between about 1200 mL/m$^2$ and about 1500 mL/m$^2$. By contrast, conventional fluid bladders typically have a low fluid volume relative to the treatment area or a very high fluid volume relative to the treatment area. In one example of a conventional liquid bladder, the fluid volume/treatment area ratio is well below 1000 mL/m$^2$ at 10 psi, and in one example, 800 mL/m$^2$. In another conventional example, the fluid volume/treatment area ratio is over nearly 3000 mL/m$^2$ at 5 psi, nearly 4000 mL/m$^2$ at 10 psi and nearly 4500 mL/m$^2$ at 15 psi. Moreover, because conventional liquid bladders aim to have generally uniform dot connection distributions (and likewise fluid channel size), conventional bladders fail to realize the many benefits of selective reinforcement described herein even if the total fluid volume is changed.

As explained above, the fluidic channel width informs the cross-sectional area of the fluidic channel, which affects flow rate, pressure, and other parameters. In an exemplary case utilizing dot patterns, the channel width is based on the positioning and spacing of dots. One will appreciate that even small changes in the dot spacing and diameter can have large effects on the fluid flow. For example, even if the height remains the same, a small change in the fluidic channel width has a relative large effect when multiplied by the number of fluidic channels. Thus, the dot spacing and dot diameter may be critical to optimizing performance.

As explained above, the edge-to-edge spacing of the dots (e.g. d1 in FIG. 4) generally corresponds to the fluidic channel width. In various embodiments, the average edge-to-edge spacing between adjacent dots in a kink-resistant zone is between about 0.35 inch and about 0.75 inch, preferably between about 0.35 inch and about 0.5 inch, and more preferably 0.425 inch. In various embodiments, the average edge-to-edge spacing between dots in a kink-resistant zone is 0.235 inch. In various embodiments, the average center-to-center spacing between dots in a kink-resistant zone is between about 0.15 inch and about 0.5 inch, preferably about 0.2 inch and about 0.5 inch, more preferably between about 0.2 inch and about 0.25 inch, and more preferably about 0.155 inch. In various embodiments, average spacing between dots in the remainder of the fluid bladder aside from the kink-resistant zone is less than about 0.35 inch, and preferably about 0.33 inch.

As used herein, "adjacent dots" generally refers to dots immediately adjacent one another. The dots may be oriented laterally or longitudinally (e.g., FIG. 4) or diagonally. In various respects, "spacing" refers to the minimum distance between the dots.

In summary, the exemplary wrap of FIG. 1 is configured to reduce or eliminate kinking during use. The exemplary wrap provides a kink-resistant zone wherein the regular pattern of attachment points is interrupted. In the open areas of the fluid bladder, attachment points may be formed as disclosed by U.S. Pat. No. 6,695,872 to Elkins. In the Elkins wrap, the matrix of connections, attachment points and curvilinear fences, acts to disperse the liquid throughout the bladder and redirect the flow of a liquid as necessary. In various embodiments, the same principles are used to guide the design of dot connections in the open areas of wrap 30. In various embodiments, the exemplary wrap 30 has dots formed in a triangular grid in open areas 70.

By contrast, the exemplary wrap has a dot configuration to increase kink resistance in kink prone regions. In various embodiments, the attachment points of wrap 30 have an irregular pattern and configuration in a kink resistant zone. In this kink-resistant zone, the attachment points are arranged differently than in the remainder of the wrap. The exemplary wrap is reinforced by dimensioning, positioning, and configuring the attachment points to resist kinking in the selected local zone(s) as described herein. Any of the above ranges—dot diameter, dot spacing, volume/surface ratio, and the like—may be used in any combination in accordance with the invention.

The reinforced wrap in accordance with the above provides several advantages over conventional wraps with dot patterns. For one, the wrap may realize the advantages of a uniform distribution of dots in open areas (e.g., effective redirection of fluid flow) while reducing the risk of kinking in selected areas. The selective distribution and configuration of dot connections may increase flow in open areas while maintaining efficient flow in kink-prone areas even when placed in compression and/or bent. The wrap in accordance with the invention may also have improved fluid circulation and performance. Specifically, the wrap may avoid undesirable cold spots, negative flow turbulence, and/or fluid blockages in comparison to existing wraps.

An exemplary use of a modular therapy apparatus in accordance with the invention will now be described with reference to FIG. 1. This example is provided for illustration and is not intended to limit the scope of the invention. Exemplary wrap 30 is shown in the open state in FIG. 1. The open wrap is positioned adjacent a portion of a human patient's leg requiring treatment. The exemplary wrap includes a fastener so the wrap can be rolled and coupled around the leg in a manner similar to that described in U.S Patent Pub. No. 2005/0256556, the entire contents of which are incorporated herein for all purposes by reference.

The wrap is then connected to control unit 39. The exemplary control unit includes a mechanism for cooling and circulating a liquid coolant. The exemplary control unit includes a fluid reservoir for containing ice water and a pump. In a practical realization of this embodiment, the liquid is cooled tap water and the gas provided to gas pressure bladder 38 is air. The liquid for fluid bladder 37 is cooled by placing ice into an ice box portion of the control unit, resulting in temperatures ranging typically between about 32° F. and about 50° F. In various embodiments, the liquid is supplied to the fluid bladder at a pressure in the range between about 5 psi and about 20 psi, between about 10 psi and about 20 psi, between about 15 psi and about 20 psi, or at an average of about 19 psig.

The user turns on the control unit and selects desired settings to circulate fluid to fluid bladder 37. In the exemplary case, the control unit receives and recirculates liquid returned from the fluid bladder. The control unit is also capable of controlling the temperature of the liquid to the fluid bladder.

The exemplary control unit also includes an air pump and controller. Air is pumped into gas pressure bladder 38 and the pressure in the bladder is controlled by the control unit thereby regulating compressive pressure on the fluid bladder. The pressure of air furnished by the control unit is generally between about 0 to about 2 psig, and preferably between about 0.25 to about 1.5 psig. As a result of the exemplary selective reinforcement dot pattern, the wrap can operate at lower fluid volumes, lower fluid pressure, and/or increased compressive force without a commensurate risk of kinking.

It should be noted that the invention is applicable to many other types of therapy components, and the particular liquid, its temperature, and pressure will be dependent upon the design and purpose of such therapy components. This is also true of the air pressure, and in some instances, it is cycled between two pressures.

Typically, the treatment area of the wrap will range from about 0.15 sq.-feet to about 6 sq.-feet. In the case of a knee application as described above, this area will be about 3 sq.-feet. In the case of an elbow, this area will be about 1 sq.-feet to 1.5 sq.-feet. In turn, one will appreciate from the description herein that the size and shape of the treatment area and fluid pathway influence the desired inlet temperature and flow rate settings, among other settings.

FIGS. 5 and 6 illustrate wraps and constituent components having various shapes to accommodate different animate body contours. FIG. 5 illustrates a wrap 30b configured for applying to a body of a canine. Wrap 30b is similar in many respects to wrap 30 described above except that the fluid bladder, gas pressure bladder, and sleeve have a shape to accommodate a canine body or body part. The peripheral border is modified to enable wrapping to the body, in the exemplary case a four-flap, cloverleaf-type shape. Each of the flaps are shaped to wrap around the canine body part.

Wrap 30b includes a dot matrix similar to wrap 30 described above. A fence 62b extends through a central interior of the wrap to define a fluid pathway that snakes around the periphery of the wrap. A peripheral fence 62b' extends around the wrap border. Both fences have a generally curvilinear shape. As shown in FIG. 5, dots 65b cover the entire fluid bladder.

Unlike wrap 30, however, wrap 30b has a considerably smaller area and thus does not have any significant and discernible open areas. For this reason, the dots are configured to form a selectively reinforced region that comprises a large portion or all of the fluid bladder. In particular, the kink-prone regions generally are located around the slits defining adjacent edges of the flaps, and especially the apex of the slits positioned inward of the border.

As will be understood from the figure and description above, a wrap may have several kink-prone regions having different relative levels of risk of kinking. The central region 62b of the exemplary wrap is especially prone to kinking because the material width is narrowed and subject to considerable bending, referred to as a "necking" region. The amount of area to accommodate bending in the central region is also divided by fence 62b. The central region also tends to undergo twisting and bending in more than one direction. The material adjacent the flap edges but further towards the outer periphery, however, generally has a lower relative propensity to kink.

As shown in FIG. 5, the dots in the central region have a skewed pattern that avoids or reduces the probability of hinge lines forming near the center, generally designated 81, which is a high stress concentration area. Instead, stresses that build during bending find their way along dots away from the narrowed central region.

In various embodiments, the selectively reinforced dot pattern is configured to increase the local tensile strength by at least about 10%, and more preferably at least about 20%, at least about 50%, at least about 75%, at least about 100%, or at least about 150%. In various embodiments, the selectively reinforced dot pattern is configured to increase resistance to kinking by at least about 10%, and more preferably at least about 20%, at least about 50%, or at least about 75%, at least about 100%, or at least about 150%. In various respects, resistance to kinking refers to the occurrence of measurable kinking or kink failure during use. In various embodiments, the selectively reinforced dot pattern is configured to reduce the risk of kinking by at least about 10%, and more preferably at least about 20%, at least about 50%, or at least about 75%.

FIGS. 6 and 7 illustrates a wrap 30c configured for applying to a human. Wrap 30c is similar in many respects to wrap 30 described above except that the fluid bladder, gas pressure bladder, and sleeve have a shape to accommodate application on a human shoulder. Accordingly, the wrap has a more complex shape.

FIG. 7 is an enlarged detail view of one of the primary regions otherwise prone to kinking. As discussed above, for purposes of illustration of the principles herein, exemplary wrap 30c includes a series of dots in this region, some of which have conventional positioning (e.g. line "A") and some of which have positioning to reduce the likelihood of kinking (e.g., line "B"). Line "C" illustrates the natural hinge line determined by the shape of the wrap. The exemplary non-linear positioning of the dots of line "B", reduces the likelihood of bending focusing along line "B". Instead, the bending stress will find a path along dots that are directed towards an open area. By contrast, bending is likely to occur along linear line "A".

FIG. 8 illustrates another wrap 30d in accordance with aspects of the invention. Wrap 30d is similar in many respects to wrap 30 except that wrap 30d includes a separate and distinct structural member to provide selective reinforcement instead of a variation in the weld pattern, materials, and the like.

Wrap 30d includes a fluid bladder 37d and one or more reinforcement members 101. The fluid bladder includes an inlet 42d and outlet 44d. A heat exchanging fluid from a reservoir is introduced to the bladder through the inlet, typically using a pump. Exemplary outlet 44 is connected to the reservoir so fluid is returned and recirculated.

In various embodiments, reinforcement member 101 is attached to a side of the fluid bladder opposite from the bladder's treatment side. In an exemplary embodiment, reinforcement member 101 is positioned between fluid bladder 37 and gas pressure bladder 38. The reinforcement member may be integrated with or attached to one side of middle layer 35 (shown, e.g., in FIG. 3). In an exemplary embodiment, the reinforcement member is attached to a gas side of the middle layer and actually disposed within what becomes the gas pressure bladder. In various embodiments, the reinforcement member is carried by a substrate in a reinforcement layer. The optional reinforcement layer is assembled within the wrap similar to the first, middle, and second layers.

FIG. 3 shows an exemplary positioning of reinforcement member 101. In the exemplary wrap of FIG. 3, a reinforcement member is positioned within gas pressure bladder 38. In the exemplary configuration, if the gas pressure bladder is collapsed, the reinforcement member will be placed in compression and prevent total closure of the gas channel. Instead, the edges of the reinforcement member will retain some space for the gas to flow through the bladder thus preventing total blockage. The reinforcement member may be carried on a substrate that has a width corresponding to the pressure bladder to enable relative positioning of the reinforcement member in the bladder.

FIG. 8 illustrates a wrap 30d with several kink-resistant zones 73d including separate reinforcement members 101. The exemplary reinforcement members have elongated shapes and are essentially aligned with a direction of flow. One of the reinforcement members is essentially straight. The others have an irregular shape with curves, corners, and the like.

The reinforcement members may have a variety of shapes and sizes. The exemplary reinforcement members 101 are substantially planar to facilitate attaching to the fluid bladder and maintain a lower profile of the wrap. The thin shape may also reduce wrinkling in the wrap. However, one will appreciate that the reinforcement members may have a three-dimensional shape with a thickness such as a rod, a bar, a box, and more.

The reinforcement members 101 generally impart increased strength to the local region where they are positioned. In various embodiments, the reinforcement members have a bending stiffness or tensile strength at least an order of magnitude higher than the fluid bladder. In various embodiments, the reinforcement members are configured to increase the local tensile strength of the resulting wrap by at least about 10%, and more preferably at least about 20%, at least about 50%, at least about 75%, at least about 100%, or at least about 150%. In an exemplary embodiment, the reinforcement member has a significantly higher hardness (durometer) than the sleeve, fluid bladder, and/or gas pressure bladder. In an exemplary embodiment, the sleeve comprises nylon with a skim coat or vapor barrier and the fluid and gas pressure bladder comprise urethane with a stiffener (e.g., nylon). In turn, the exemplary reinforcement member has an increased thickness, higher material strength, or both. In an exemplary embodiment, the reinforcement member has a thickness comparable to the bladder materials and is formed of a high nylon content material.

In various embodiments, the wrap includes a reinforced dot pattern and a discrete reinforcement member. A region of the reinforced dot pattern may be positioned in various ways with respect to the one or more reinforcement members. The reinforced dot pattern region may be larger than the reinforcement member, the same size, or smaller. The reinforced dot pattern region may overlap the reinforcement member. The reinforcement member may overlap the reinforced dot pattern region. The reinforcement member and reinforced dot pattern may be aligned and positioned in the same region.

In various embodiments, the chambers of the fluid bladder and gas pressure bladder comprise primarily flexible materials and the reinforcement member is a formed of a rigid material. The exemplary wrap 30d includes a sleeve forming of flexible nylon loop material, a fluid bladder and gas pressure bladder formed of polyurethane-based materials, and a reinforcement member formed of metal. Suitable materials for the reinforcement member include, but are not limited to, metals, alloys, thermoplastics, ceramics, shape memory materials (e.g., nickel titanium), open cell foam, "scrubby pad", and more.

In some respects, the reinforcement members may be similar in shape, structure, and overall design to reinforcements in other fields. For example, the reinforcement member may have a waffle shape, I-beam shape, or cross-beam to achieve the desired amount of structural strength.

In various embodiments, the reinforcement member is shaped and configured based on the anatomy of the body part. For example, in the case of a knee wrap, the reinforcement member may have a curved shape to better conform to the knee when bent. In this case, the curve may have an arc angle to allow bending to a predetermined angle but resist further local bending, for example, past a minimum bend radius (kink radius). In the example of a knee wrap, a reinforcement member positioned around the knee may be used to promote a more uniform bend or curve and prevent wrinkle-type kinks.

In various embodiments, reinforcement member 101 is a batten. The batten may be flexible in one direction of bending and rigid in another direction. In another embodiment, the reinforcement member is an adhesive. In this case, the fluid bladder is bonded to another member have a high tensile strength in a manner that prevents shearing of one member relative to another thereby resisting bending. In other words, as the flexible bladder is bent, the other material counteracts the bending force of the inner bladder material as it is pulled in tension and limits the bend radius. The reinforcement member may be one or more of a batten, a weakened section or line, an exoskeleton, a ribbon, a tubular member, a helical member, a spring, a bar linkage, and the like. In the example of an exoskeleton, the reinforcement member may include a rigid frame or skeletal structural to increase the rigidity and/or bending strength of the selected region in which it is placed. The member may be shaped so it is positioned around the dots in the bladder. Thus, the reinforcement member may be placed in the mold before forming the dots and fences. One of skill in the art will appreciate from the description herein the manner for selecting materials and configuring the reinforcement member to achieve the desired level of reinforcement.

In the exemplary embodiment, each of reinforcement members 101 is positioned entirely within or along a fluidic channel 48d. The members, however, may also overlap multiple channels. This may be desirable where the kink-prone region relates to a feature that risks kinking in multiple fluidic channels or fluid pathways. For example, in the case of a knee wrap, the apex of the bend corresponding to the knee cap may overlap multiple fluid pathways.

Figure 9:
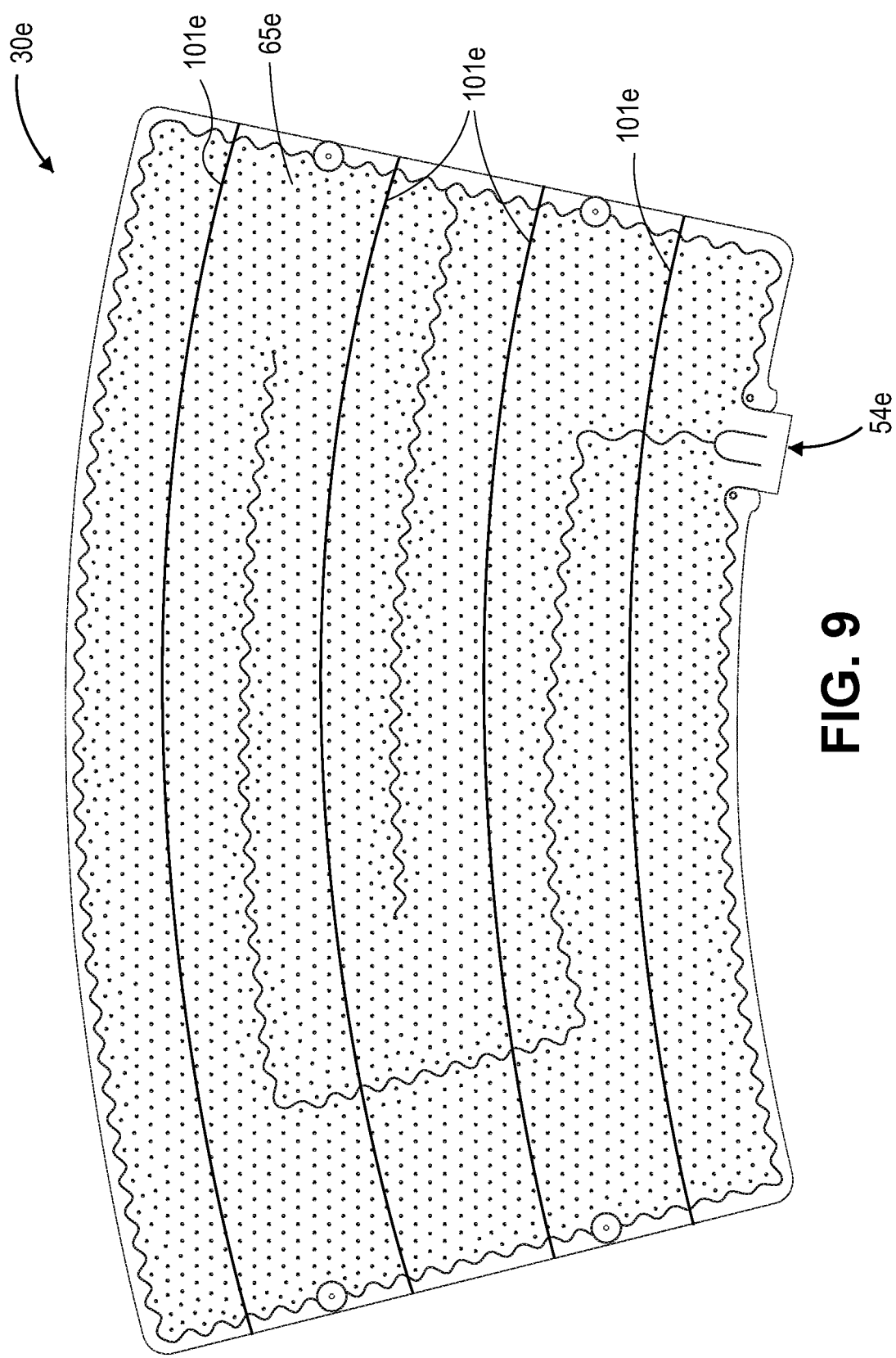
FIG. 9 is a top plan view of another selectively reinforced therapeutic wrap similar to the wrap of FIG. 8, illustrating use of four reinforcement members configured to provide kink resistance during operation.

FIG. 9 illustrates a wrap 30e configured and constructed similar to the wrap 30d described above and shown in FIG. 8. Wrap 30e includes four reinforcement members 101.

The exemplary reinforcement members are strips welded or bonded to the gas pressure bladder. The exemplary strips comprise stiffened urethane. The exemplary reinforcement members have essentially the same bending strength, but one will appreciate that they may have different strengths. Moreover, each reinforcement member may have a different or variable bending strength along its length.

Each of the exemplary reinforcement members spans the entire width of the wrap from border-to-border and is generally aligned within a lateral fluid flowpath 50. Likewise, the reinforcement members are parallel to the direction of wrapping. Alternatively, the reinforcement members may have a serpentine shape that corresponds to the serpentine fluid flowpath. The exemplary wrap is designed to wrap around a straight body part like a leg. When the wrap is fastened to the body part, the reinforcement members form circular rings around the body part. Accordingly, the reinforcement members selectively reinforce the flowpath and resist bending in a transverse direction to the flowpath. Similarly, the reinforcement members may be configured to resist bending (increase tensile strength) in one or two bending directions but not in the other directions.

In operation and use, wraps 30d and 30e of FIGS. 8 and 9 having reinforcement members are used in a similar manner to wrap 30 described above. A user applies the wrap to the body part to be treated. The wrap is connected to a reservoir, pump, and other system components. The user then turns on the system to flow fluid to the wrap for therapy.

One will appreciate from the description above various techniques for increasing the bending strength and resistance to kinking in selected regions of the fluid bladder, and in various respects, the therapeutic wrap. As described above, the kink-resistant features are confined to a specific region of the fluid bladder. The positioning and area of a selective kink-resistant zone may depend on whether it is desirable to reinforce a specific fluid pathway or a general region of bending in the bladder. In various embodiments, the kink-resistant features are aligned within a fluidic channel or fluid pathway. In various embodiments, the kink-resistant features are aligned entirely within a fluidic channel or fluid pathway. In various embodiments, the kink-resistant features overlap multiple fluidic channels or fluid pathways.

In various embodiments, the kink-resistant zone is distal from the inlet and the outlet. As shown in FIGS. 5 and 6, for example, dot connections immediately adjacent inlet and outlet manifold 54 have regular dot patterns forming an essentially equilateral triangular pattern.

In various embodiments, the fluid bladder and/or wrap includes a kink-resistant zone employing any combination of the above features. In various embodiments, the fluid bladder and/or wrap includes a plurality of kink-resistant zone employing any combination of the above features. The kink-resistant zones may be spaced from each other or directly adjacent one another. The features of the kink-resistant zones may be contiguous but separate elements. The features of the kink-resistant zones may be integrally formed thereby forming an integrated kink-resistant zone. In various embodiments, a sleeve and/or reinforcement layer embodying any of the features described herein is provided.

A method of making and assembling the selectively reinforced therapeutic wrap in accordance with the invention will now be described. The wrap may be manufactured using the techniques described above and known in the art in accordance with the description herein.

For illustrative purposes, the method of manufacturing a wrap similar to that shown in FIG. 9 will be described. One will appreciate that the method may be modified to manufacture any of the wraps and heat exchange devices described herein. For example, the method may be modified to manufacture a heat-exchanging fluid bladder without a gas pressure bladder or sleeve.

Figure 10B:
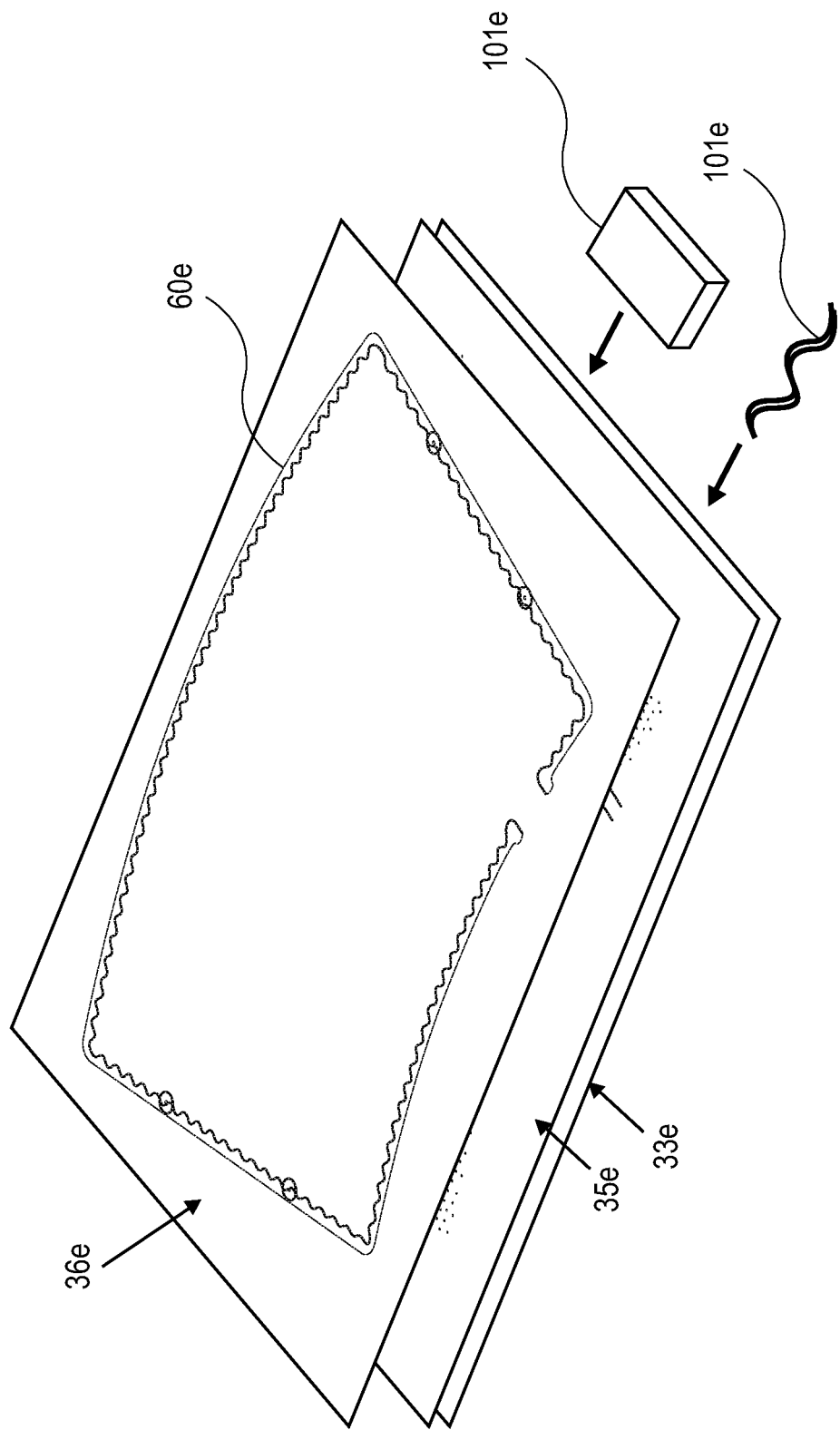
Figure 10C:
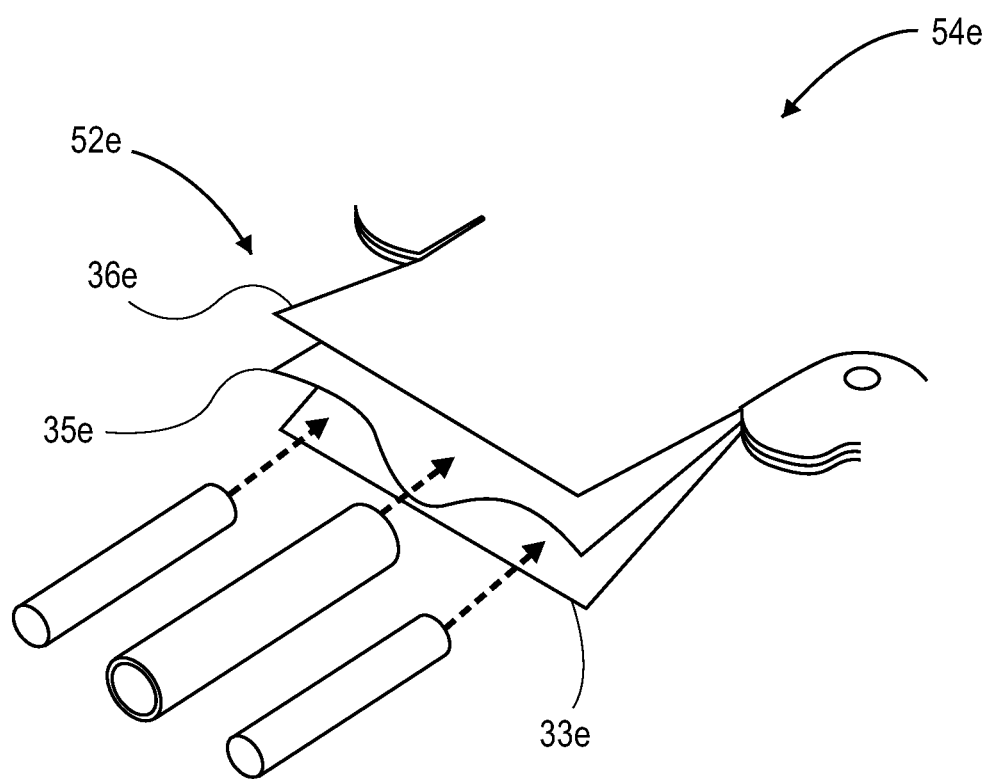
Figure 10D:
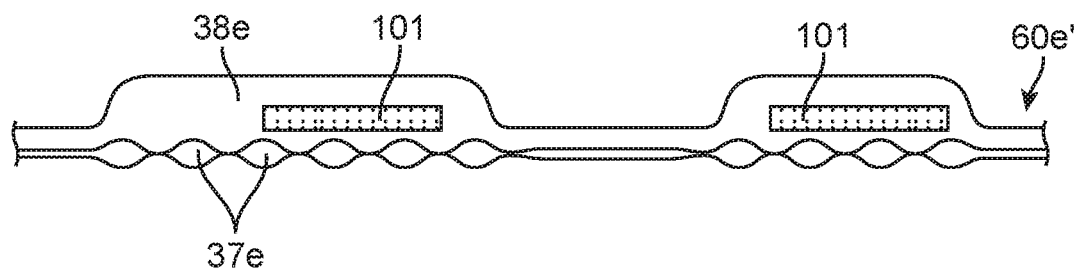
FIGS. 10D, 10E, 10F and 10G illustrate an embodiment of a therapeutic wrap with a reinforcement member disposed in a gas bladder.

FIGS. 10A, 10B, and 10C illustrate the general process for manufacturing a wrap similar to that shown in FIG. 9. The exemplary wrap includes reinforcement members 101 positioned adjacent middle layer 35e and in the gas pressure bladder 38e.

FIG. 10A illustrates a dot layer processing operation. The first outer layer 33e is aligned with a middle layer 35e. The sheets of material are sealed together at dot connections 65e and at interior fences 62e thereby forming the basic outline of the fluid flowpath and fluidic channels. At a later time, wall 60e' is welded to other walls 60e along the perimeter to form the fluid bladder. The dot connections and fences are generally prepared using conventional techniques. In one embodiment, the connections are formed by RF welding.

The exemplary materials for the gas pressure bladder and fluid bladder are made of a nylon material coated with polyurethane to provide both the RF welding qualities and the needed liquid or air impermeability.

In one embodiment, the bladders can comprise fabrics (e.g., nylon fabric) that are laminated with asymmetric amounts of polyurethane. For example, the inner surface of the outer wall of the coolant chamber may have an extra heavy coating. In one example, the outer coating comprises about 5 oz of polyurethane while the inner surfaces of the other walls have standard coatings corresponding to about 3 oz of polyurethane. Accordingly, the surfaces of the inner wall of the coolant and air chambers and the inner surface of the outer wall of the air chamber have standard 3 oz coatings. This construction only requires one non-standard fabric (the fabric having the 5 oz coating), while providing the extra polyurethane necessary to produce an extremely robust weld capable of taking or withstanding over 25,000 cycles at 30 psi. This construction can reduce manufacturing costs. It also facilitates using a lighter weight fabric, which can result in a more flexible heat exchanger that can better fit to the body.

In another embodiment, the inner wall of the coolant chamber has a 5 oz coating of polyurethane in order to facilitate a yet stronger bond at the expense of increased manufacturing costs due to the use of a second non-standard fabric. A finish on the nylon material can also provide a permanent antimicrobial finish to prevent mold growth.

FIG. 10B illustrates a fence layer of the manufacturing process. In FIG. 10B, reinforcement members 101 are positioned over middle layer 35e and affixed with common techniques such as epoxy or welding. The reinforcement members are aligned with the fluid flowpaths in the desired locations.

Next, second outer layer 36e is positioned over the sealed first layer 33e and middle layer 35e. As shown in FIG. 10B, the exemplary three sheet layers have essentially the same shape to enable easy alignment. With the three layers and reinforcement members in position, all the layers are sealed together along a common border and peripheral fence 62e. The sealing along the common border simultaneously forms the gas pressure bladder and fluid bladder. A space is left in the common border to accommodate the inlet and outlet ports for the bladders.

The reinforcement layers may be assembled in various other ways. In various embodiments, the wrap includes a reinforcement layer having a substrate supporting one or more reinforcement members in selected locations. The substrate enables easier assembly, in part, by making it easier to align the reinforcing member or members with the fluid bladder and gas pressure bladder. The substrate and reinforcing member may be joined together permanently, removable, or otherwise separate. In various embodiments, the substrate dimensions correspond to the fluid bladder periphery and inner dimensions of the sleeve such that the reinforcing layer can be aligned simply be inserting it into the sleeve pouch next to the fluid bladder. In the exemplary wrap, the substrate is dimensioned to be applied over the fluid bladder whereby the reinforcing member or members align with the desired fluidic channels.

Similarly, the reinforcement layer and/or reinforcement members may be formed concurrently with the bladder. Other manufacturing techniques include, but are not limited to, spraying, molding, silk screening, and adhesives. One will appreciate that manufacturing techniques common in the polymer and semiconductor fields may also be used such as etching, deposition, and lithography. Further details regarding the components and manufacturing techniques that may be used are disclosed in U.S. Pat. No. 7,198,093 to Elkins, the entire contents of which are incorporated herein for all purposes.

Turning to FIG. 10C, after forming the bladders, excess material outside the common border is removed and manifold 54 is formed. Exemplary gas pressure bladder 38e is formed with a single opening and fluid bladder 37e is formed with two openings to receive the tubes in the orientation shown in FIG. 10C. A tube, such as a polyurethane tube, is positioned in each one of these openings and then welded to a respective bladder to form a fluid tight seal therewith. The tubes extending from the bladders typically have an inner diameter of about ⅛ inch. The manifold passageways typically have a diameter of about ¼ inch. Manifold 54 can be inserted into the tubes to form a seal therewith. For example, each manifold tubular member end portion that mates with or is inserted into a respective tube extending from one or the other bladder can be provided with tapered hose barbs to enhance the seal as is well known in the art. Further details regarding the manifold construction are disclosed in U.S. Patent Pub. No. 2009/0005841 to Schirrmacher et al., the entire contents of which are incorporated herein for all purposes by reference. A fluid circulation control unit as diagrammatically represented in FIG. 1 and generally designated with reference numeral 39 is coupled to manifold 54 with tubing to fluidly communicate the therapy fluids to bladders 37 and 38.

Although described in terms of a three-layer, dual-bladder design, one will appreciate that the wrap and therapy system in accordance with the invention may have other variations and modifications. In one example, although the wrap and therapy system described above generally has been described with a dual bladder design, a single bladder heat exchange device can be used.

In another embodiment, the wrap in accordance with the invention is selectively reinforced by subjecting a selected portion of one or both of materials 33e and 35e to stretching or pre-tensioning. One of skill in the art will appreciate that if one side of the bladder 37e is stretched relative to the other, the bladder will tend towards a curved shape. Likewise, selective pre-tensioning will form a selective contour. In various embodiments, the pre-tensioning is performed to form a predetermined curve in the resulting bladder that has a propensity to wrap around a body part. The predetermined curve may have a radius slightly larger than the body part so it provides a degree of tension when wrapped while also reducing the risk of kinking.

Alternatively, the resulting bladder may be formed in a substantially flat shape with one wall or a portion of the bladder under stress (tension). The tension is then relieved when the bladder is forced around a body part. For example, one of the sheet materials may be tensioned but held in a flat condition by the joining to the other sheet material. In another example, the bladder may include a reinforcement member to hold the resulting bladder in a flat condition.

The pre-tensioning may be performed in an otherwise conventional manner as will be understood from the description herein. For example, the material or materials may be placed in a mold and elongated or stretched. The material may also be heated to expand the dimensions and assembled while still expanded. The material may be anisotropic.

In an exemplary embodiment, a selected portion of first material 33e in a kink-resistant zone is subjected to pre-tensioning. Alternatively, pre-tensioning may be applied to an entire layer of material. While the material remains in tension it is attached to middle layer 35e. The attachment may include forming a dot pattern, fence layer, and the like as described above. The attachment may also be in an otherwise conventional manner. Next the second outer layer is attached to the middle layer and the manufacturing process is carried out as described above.

In the exemplary embodiment, the second outer layer and/or attachment connections keep the finished wrap in a generally planar state. When the wrap is placed around a curved body part, however, the tension in the pre-stretched kink-resistant zone is relieved. In this manner, the risk of kinking of the material is reduced without the need for a specially-configured dot pattern or external reinforcement member. In various embodiments, heating is performed in addition to or in place of pre-tensioning.

The above process may be modified. For example, the first and second bladder may be formed simultaneously while the first material is pre-tensioned. Additionally, the middle layer and second layer may include a selected pre-tensioned region instead of or in combination with the first layer.

FIGS. 10D-G illustrate an embodiment of a reinforcement member 101 which can be disposed within the gas pressure bladder to prevent or reduce kinking in the gas bladder 38e. The reinforcement member 101 can be a foam or sponge-like material having an open cell or porous structure that is gas permeable and allows the passage of a gas through itself while keeping the gas bladder 38e open. In some embodiments, the reinforcement member can also be of a spacer fabric, mesh or non-porous material. The reinforcement member 101 can be positioned along locations which are prone to kinking, such as at portions of the wrap 30 that are folded or bent to conform to the patient's anatomy and/or to secure the wrap and/or are subject to flexure. For example, for a knee wrap, the portion of the wrap around the knee joint undergoes joint flexure, which can cause kinking of the wrap around the knee. By placing one or more reinforcement members 101 in the gas bladder around the portion of the wrap that is wrapped around the knee joint, kinking in the knee joint area is prevented or reduced by allowing the gas to vent thru the porous structural member, and/or around the edges of the structural member. Other kink prone areas include the transition area of the wrap between the main body portion of the wrap and the various arms and/or wings of the wrap. The performance may be further enhanced by providing the reinforcement member in most of or the entire portion of the wrap. Further benefit may be added if the structural member has insulating properties to reduce ambient heat transfer. Therefore, in some embodiments, the reinforcing member can be an insulator or an insulating material. In some embodiments, an insulating reinforcing member can have an adhesive coating at least the side of the reinforcing member facing the fluid bladder in order to improve contact between the insulating reinforcing member and the middle layer of the fluid bladder, thereby improving the insulation of the fluid bladder.

The reinforcement member 101 can be provided in a variety of shapes and sizes. For example, in some embodiments, the reinforcement member can be donut or washer shaped, such that the reinforcement member can have a center hole for attaching and securing the reinforcement member within the air bladder. For example, a spot weld can be placed within the center hole to secure the reinforcement member in place. In other embodiments, the reinforcement member can have other shapes, such as an hourglass shape, an oval shape, an arc shape, a wavy or undulating or sinusoidal shape, a generally curvilinear shape, for example, as illustrated in FIGS. 10H and 10I. In some embodiments, the shape of the reinforcement member is defined by the surrounding and/or underlying structures in the gas bladder and fluid bladder. For example, the perimeter or border in the gas bladder formed by the peripheral fence 62e can define a portion of the shape and size of the reinforcement member 101. In addition, interior fences 62e, which can be disposed within the gas bladder and/or the fluid bladder, can also define the shape and size of the reinforcement member 101. Other perimeter and interior features, such as attachment points and welds in the gas bladder and/or fluid bladder can also be used to define the size and shape of the reinforcement member. In other embodiments, the reinforcement member can be square, triangular, rectangular, hexagonal, or generally rectilinear shaped. In other embodiments, the reinforcement member can be shaped and sized to match the shape and size of the portion of the air bladder to be reinforced. These alternatively shaped reinforcement members can also have one or more holes so that the reinforcement member can be spot welded in place. In other embodiments, the reinforcement member can be spot welded or otherwise adhered or fastened directly to the layers that form the gas bladder rather than spot welding the layers together through a hole in the reinforcement member.

In some embodiments, the reinforcement member 101 can be substantially smaller than the air bladder such that a plurality of reinforcement members can be placed in the kink prone area of the air bladder. For example, the reinforcement member 101 can be less than ⅓, ¼, ⅕, or 1/10 the width or length of the kink prone region of the air bladder. In other embodiments, the reinforcement member 101 can be approximately the same size as the kink prone region. In some embodiments, the width of the reinforcement member can be less than or approximately equal to the width of the spacing between the spot welds. In some embodiments, the width of the reinforcement member can be a multiple of the spacing distance between the spot welds.

Other techniques of fixing or staking the reinforcement member in place include use of adhesives, which can be used alone or be used in conjunction with the other forms of fixation, such as spot welding. When the adhesive is used in conjunction with another form of fixation, the adhesive may be tacky and provide releasable securement to allow repositioning of the reinforcement member before being permanently secured in place, if desired. Other fixation techniques include stitching, hook and loop fasteners, buttons, riveting, snaps, and the like. In some embodiments, the reinforcement member can be secured in place by placing fixation features around the perimeter of the reinforcement member. The fixation features can be spot welds or other guide members that hold the reinforcement member in place.

In some embodiments, the reinforcement member 101 can have a curved edge along the kink prone area in order to reduce formation of a kink along the edge of the reinforcement member 101. In some embodiments, a plurality of reinforcement members 101 can be disposed in the kink prone region. In some embodiments, the reinforcement members 101 can be disposed in a predetermined staggered or offset pattern along the kink prone region. In some embodiments, the reinforcement members can be disposed in one or more rows.

Figure 10E:
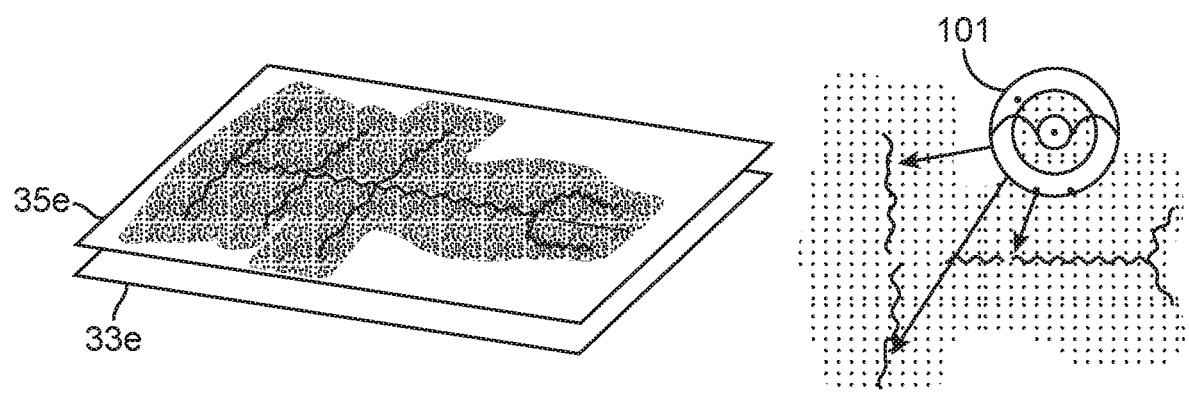
Figure 10F:
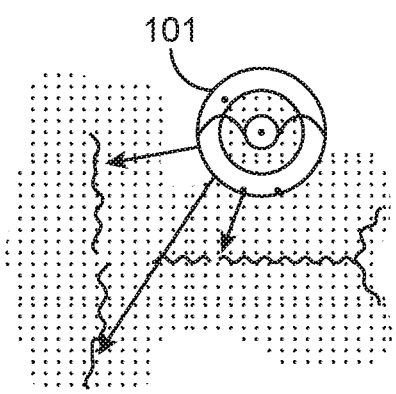
Figure 10G:
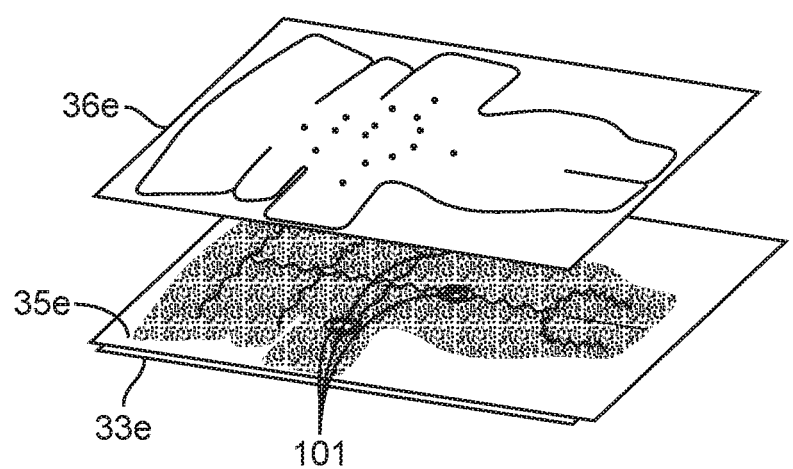
Figure 10H:
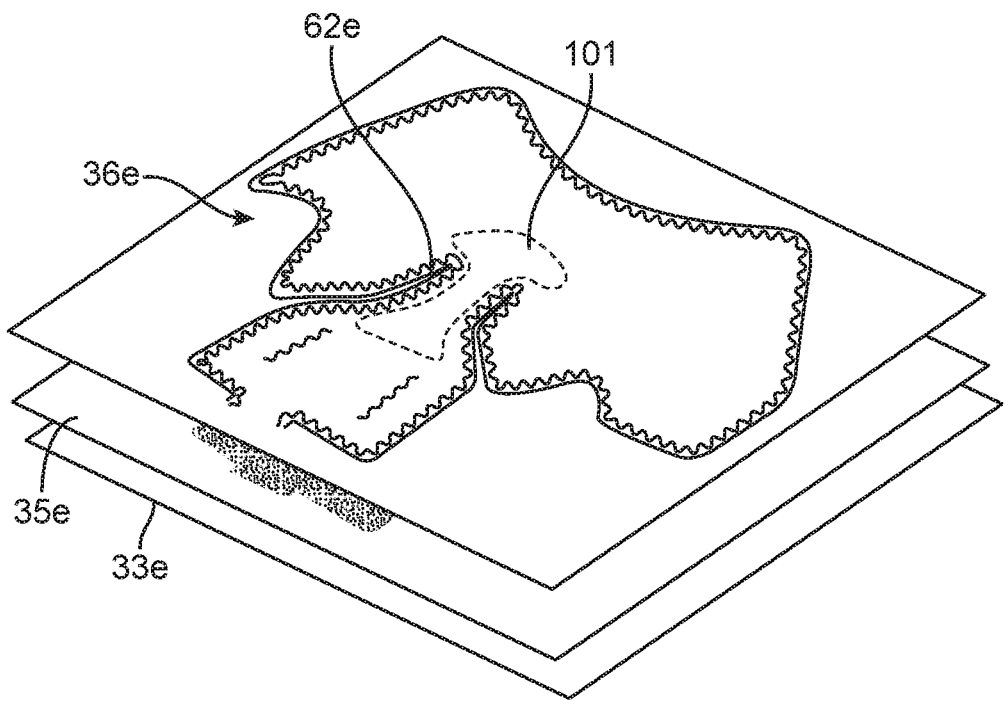
FIGS. 10H and 10I illustrate additional embodiments of a reinforcement member disposed in a gas bladder.
Figure 10I:
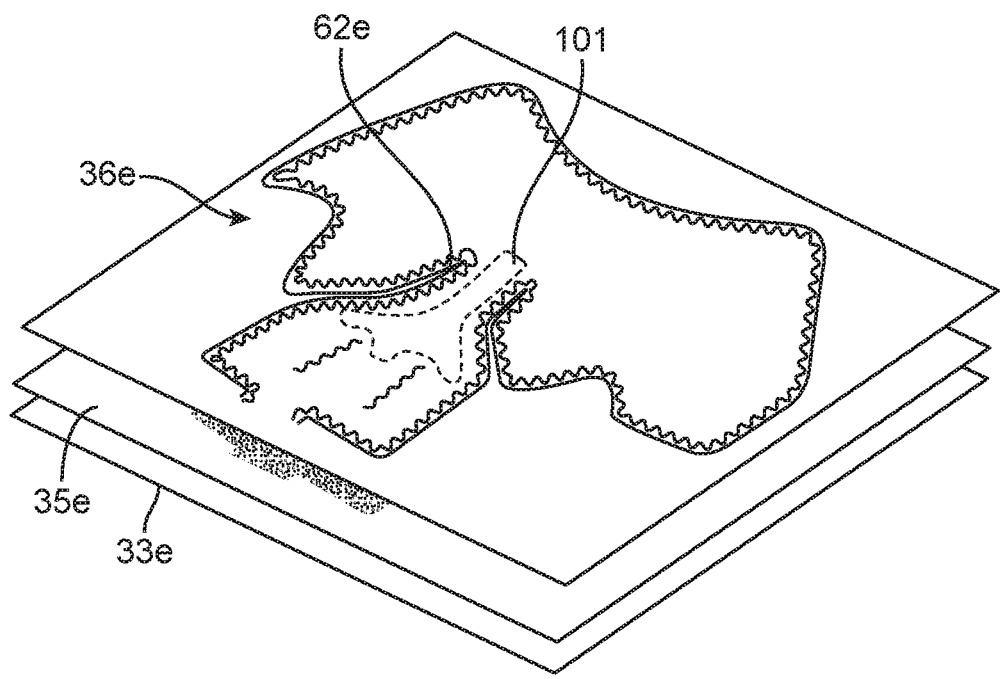

FIGS. 10E-10G illustrate one embodiment for fabricating a wrap 30 with reinforcement members 101 within the gas bladder 38e using a donut type reinforcement member 101 as described above. The first outer layer 33e and middle layer 35e can be assembled as described above to form the fluid bladder 37e. The reinforcement members 101 can then be placed at predetermined locations over remaining exposed surface of the middle layer 35e by centering the central hole of the reinforcement member 101 over placement markers, which can be weld dots in the flowpath. In some embodiments, the weld dots used as placement markers may be of different size than other weld dots, or may be of different color, or may have a marking to identify it as a placement marker. In some embodiments, a template can be used to place the reinforcement members at predetermined locations. In some embodiments, the template can have cutouts for receiving and placing the reinforcement members. In some embodiments, the reinforcement members 101 can be coated on one or both sides with a tacky adhesive that holds the reinforcement member 101 in place during the assembly process. After the reinforcement members 101 are placed, the third layer 36e can be placed over the middle layer 35e and reinforcement members to form the gas bladder 38e as described above. Welds can be made through the hole in the reinforcement member 101 to further secure the reinforcement member in place.

Figure 11:
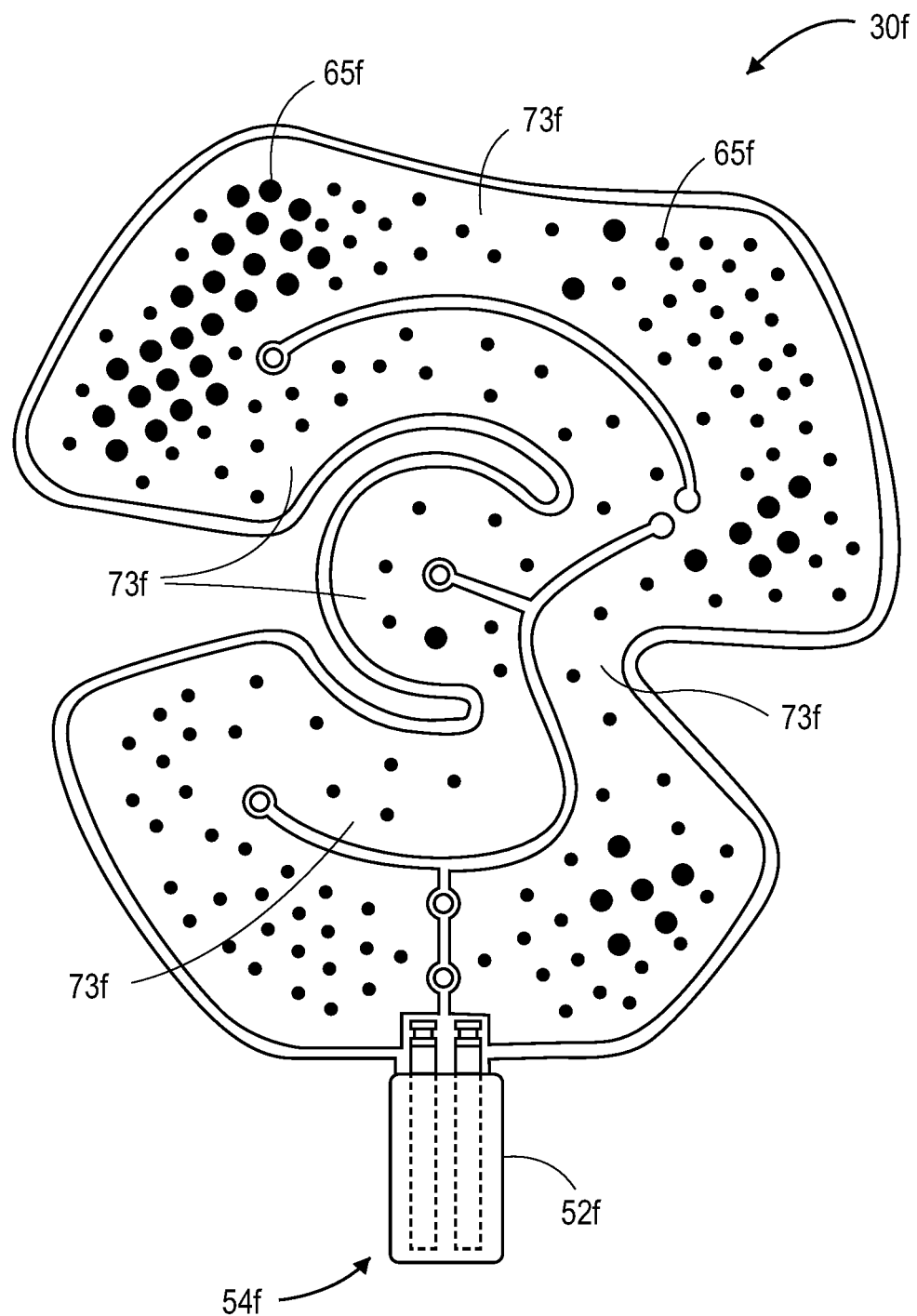
FIG. 11 is a top plan view of a selectively reinforced heat exchange device similar to the wrap of FIG. 1 for use with an elastic wrap instead of a gas pressure bladder, illustrating dot connections configured to provide kink resistance during operation.

FIG. 11 illustrates an alternative design for a temperature-controlled therapy device 30f in accordance with the invention. Device 30f is similar in many respects to wrap 30 shown in FIG. 1 except that it does not include a compressive element and sleeve. The exemplary device is a pad similar in various respects to the conventional pad described in U.S. Pat. No. 6,117,164 to Gildersleeve et al., the entire contents of which is incorporated herein for all purposes by this reference. Whereas wrap 30 includes a compressive gas bladder 38, device 30f is a single chamber pad designed to carry a liquid heat exchanging medium only. The device may be used alone or with a standard elastic wrap. For example, the device may include a fastener for attaching directly to a body part to be treated.

The exemplary fluid pad 30f is a designed to fit over a knee or shoulder. The pad includes a fluidic flowpath for promoting a desired flow even during joint flexure. In the exemplary embodiment of FIG. 11, pad 30f includes a central portion intended to be positioned over a joint.

Absent any reinforcement, pad 30f is prone to kinking because of the tortuous fluid flowpath and complex shape including many twists, sharp radiuses, and fold lines. Accordingly, pad 30f includes a dot connection matrix with selective reinforcement as described above. Indeed, exemplary pad 30f includes variable reinforcement whereby different kink-prone regions have different levels of reinforcement. As shown in FIG. 11, narrower portions of the flowpath have a dot pattern with lower distribution of dot connections than wider portions.

Dots 65f in selected kink-resistant zones 73f of the flowpath are in random alignment as described above to reduce the chance of kinking. The exemplary pad 30f has a winding fluid flowpath with a varying width. A portion of the exemplary dot pattern varies based on the flowpath. In narrow lateral sections the dots are spaced apart further. In a portion of the bladder where the flowpath makes a turn between the upwardly directed side and the laterally extending upper section, the positioning of the exemplary dots forms more of a regular repeating triangular pattern.

For illustrative purposes, portion of the wrap are shown in dots of variable diameters. In an upper left part of FIG. 11, for example, the dot diameter increases moving from the center to the left side of the pad. One will appreciate from the description herein that varying the dot diameter can allow for adjustment of strength of only a local portion of the bladder.

In another example, device 30f may include a separate reinforcement layer with rigid reinforcement members in addition to or in lieu of the selectively reinforced dot pattern configuration. As will be clear from the above example, the reinforcement layer may be a separately-formed, independent member for use with a variety of temperature-controlled therapy systems in accordance with the invention.

Exemplary device 30f thus illustrates a number of other tools for selectively reinforcing a heat exchanger in accordance with the invention. In combination with the dot spacing, dot positioning, fence configurations, and other parameters discussed above, it will be clear that the invention provides an assortment of techniques for improving performance over conventional temperature-controlled therapy devices. In various respects, the techniques described herein achieve the benefits of high kink resistance while allowing the wrap to effectively conform to complex shapes. In addition, the flow and heat exchange performance can be maintained or improved.

Various aspects of the invention are directed to a sleeve with selective reinforcement for use with conventional fluid and/or gas bladders. For example, a sleeve may be provided similar to the sleeves described above except with a reinforcement layer. The reinforcement may be configured with selective reinforcement of only a portion of the sleeve. The selective reinforcement may be in the form of a reinforcement structure positioned in only a portion of the sleeve. The reinforcement layer and/or reinforcement member may be removable. The reinforcement member has a rigidity and strength significantly higher than the sleeve material such that the sleeve resists kinking and/or bending in the selected region. In use, a plurality of sleeves with different selected reinforcement regions may be provided. A user then selects a desired sleeve and inserts one or more modular bladders. Thus, the components can be mixed and matched.

In some embodiments, the wrap can comprise only a gas bladder that can be used to provide compressive treatment of a limb or other body part. The gas bladder only embodiment can be similar to the embodiments described above except for the absence of the fluid bladder. As such, the gas bladder can be fabricated from two layers of material, rather than three. In some embodiments, the gas bladder can include features that have been described in connection with mainly the fluid bladder, such as attachment points and/or interior fences.

The above described embodiments may provide manufacturing and economic efficiencies. For example, a number of the components may be standardized and supplied off-the-shelf or sold as kits. In various embodiments, the wrap is assembled by providing a set of sleeves each with integrated reinforcement members and a pouch adapted to receive a fluid bladder, selecting one of the sleeves, and inserting a bladder into the sleeve. The plurality of sleeves may be dimensioned the same but include different selective reinforcement patterns. Alternatively, a set of different selective reinforcement assemblies, each having a substrate and one or more reinforcements as described herein, may be provided. A user may then select and a pair a reinforcement assembly with a selected sleeve and bladder. A user may also further customize the wrap by inserting, removing, and/or modifying reinforcement members.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiment whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention is further illustrated by the Examples that follow. The Examples are not intended to define or limit the scope of the invention.

EXAMPLES

Example 1

Figure 12:
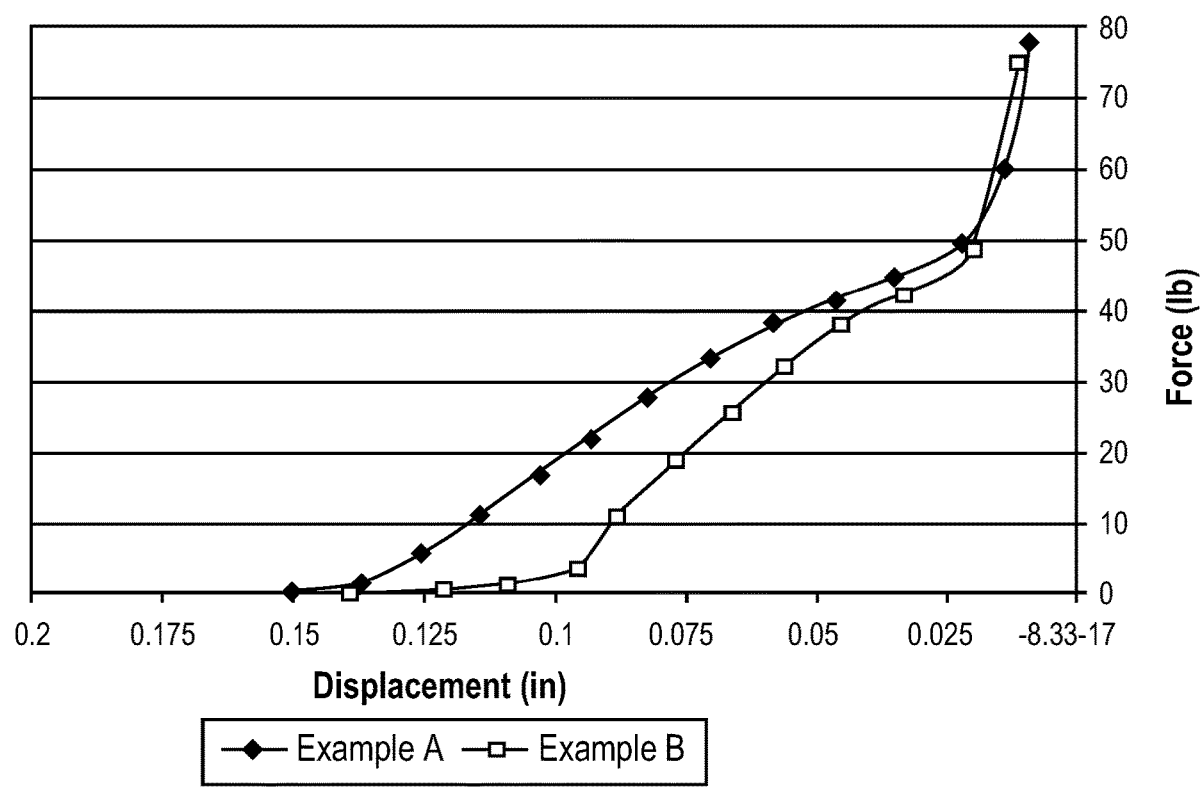
FIG. 12 is a graph illustrating force versus fluidic channel displacement at 19 psig for two exemplary wraps.

A first wrap, referred to in some respects as the "first bladder" or the "reinforced bladder" and labeled as "Example A" in FIG. 12, was prepared similar to that shown in FIG. 1. The exemplary first wrap included a repeating equilateral triangle dot pattern forming fluidic channels. The center-to-center dot spacing, which corresponds to the widths of the fluidic channels, was about 0.425". The dot diameters were between about 0.16" and 0.2".

The wrap was connected to a standard control unit and supplied with tap water from an ice bath reservoir at approximately 19 psi. The bladder was left in a flat condition in an ambient environment.

The bladder was then tested by displacing the fluid bladder with a 2"-diameter force plate in a kink-prone region. The force plate was applied to the bladder with a screw. The force applied by the bladder against the disk was measured at different levels of displacement, generally 0.010"-0.015" increments. The disk force was increased until the fluid bladder was completely occluded.

Next, a second fluid bladder, labeled as "Example B" in FIG. 12, was prepared. Wrap Example B had a similar shape and overall dimensions as the first wrap but included a conventional dot pattern. The second wrap had dots uniformly distributed in a regular triangular pattern across the entire treatment surface. The dot pattern of the second bladder comprised dots having a diameter of less than 0.15" and center-to-center spacing of about 0.33".

The second fluid bladder was connected to the same control unit and supplied with liquid at 19 psi. The same test was then conducted on the second fluid bladder. The fluid bladder was displaced with the 2"-diameter disk in the same spot as the first bladder. The force applied by the bladder against the disk was measured at the same displacement increments until the fluid bladder was completely occluded.

At about 0.14" of displacement, the first bladder exerted 1.5 pounds of force versus 0.5 pounds for the second bladder. At about 0.13", the force of the first bladder was 5.6 pounds and the force of the second bladder was only 1.4 pounds. At about 0.11", the force of the first bladder was 11.3 pounds and the force of the second bladder was only 3.8 pounds. At about 0.1", the force of the first bladder was 17 pounds and the force of the second bladder was only 10.8 pounds. At about 0.09", the force of the first bladder was 22.2 pounds and the force of the second bladder was only 19 pounds. At about 0.08", the force of the first bladder was 27.8 pounds and the force of the second bladder was only 25.6 pounds.

The complete results are shown in the graph of FIG. 12.

The test results illustrate that the force applied by the first fluid bladder was measurably higher than the second bladder at each given displacement. This force may be generally referred to as the "restorative force" or "resistive force". In some respects, all things being equal, the greater the "restorative force" the less likely it is for the fluidic channel to become kinked. Conversely, the first bladder was deflected to a lesser degree than the second bladder at each given force level. Thus, the dot spacing was critical to improving kink resistance.

The results in FIG. 12 also illustrate that the force to achieve complete displacement (occlusion) is higher in the first bladder with reinforcement.

The test results demonstrate that reinforcement in accordance with the invention increases the kinking force required to displace, and ultimately occlude, the fluidic channels. The increase in performance may be represented as the area between the two lines. This area represents an improved flow of the first bladder at the same force (pressure) levels as the conventional second bladder.

Moreover, the results in illustrate that the onset of complete occlusion failure is more gradual with the selectively reinforced bladder. The improvement in kink resistance was also shown to be attainable without a commensurate large increase in a volume of the bladder.

It is noted that the pressure range(s) for the test results of FIG. 12 are illustrative of the expected forces on the bladder during operation. The fluid was pumped to the bladders at 19 psi, which is typical for such bladder. The higher force values (e.g., 35 psi) are believed to be typical of the force levels experienced by selected kink-prone regions of the wrap when the wrap is attached to a body part and compressed. These kink-prone regions can experience pressures several orders of magnitude higher than the pump pressure.

The two bladders were also informally tested for operational effectiveness. The first bladder with selective reinforcement was found to have generally improved performance. In particular, the first bladder was found to provide one or more of the following benefits: improved heat exchange through better flow rates when in compression, reduced risk of failure from blocked fluid pathways and more even temperatures due to open flowpaths.

Example 2

Figure 13:
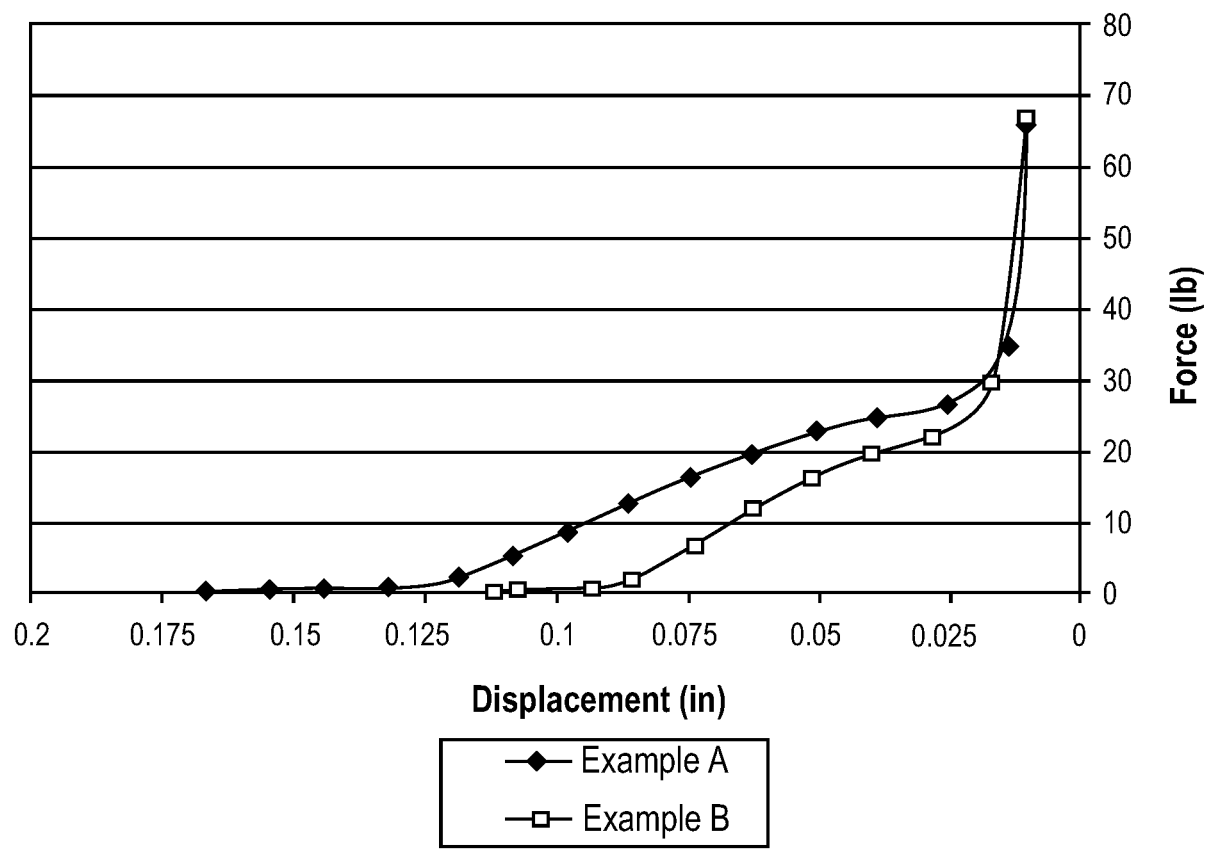
FIG. 13 is a graph illustrating force versus fluidic channel displacement at 10 psig for the two exemplary wraps of FIG. 12.

The same two fluid bladders were tested again under the same conditions except the fluid pressure was decreased to 10 psi. The results are shown in FIG. 13 where "Example A" refers to the same first bladder with reinforcement and "Example B" refers to the same second bladder without reinforcement, as described above.

Again, the results of this Example demonstrate that the force from the first bladder is generally higher at each given displacement level. In fact, as the displacement increases, the gap between the restoring force in the first bladder and the restoring force in the second bladder increases. Thus, the fluidic channels defined by the kink-resistant dot pattern in the first bladder are shown to provide increased resistance to kinking.

Example 3

The same two wraps above were provided. A third wrap having a conventional dot pattern was provided. The three wraps were filled with tap water. The water volume in the wrap per surface area of the wrap was measured versus the pressure to fill the wrap. The results are shown in FIG. 14 where "Example A", "Example B", and "Example C" are the results for the three exemplary wraps.

The bladder of Example A corresponds to the first bladder with reinforcement described in Example 1 above. The bladder of Example B corresponds to the second, conventional bladder of Example 1 above. Example C was similar to Example B in terms of relative dot spacing but had larger fluid bladder. FIG. 14 shows how volume/surface area corresponds to pressure for the three wraps.

Figure 14:
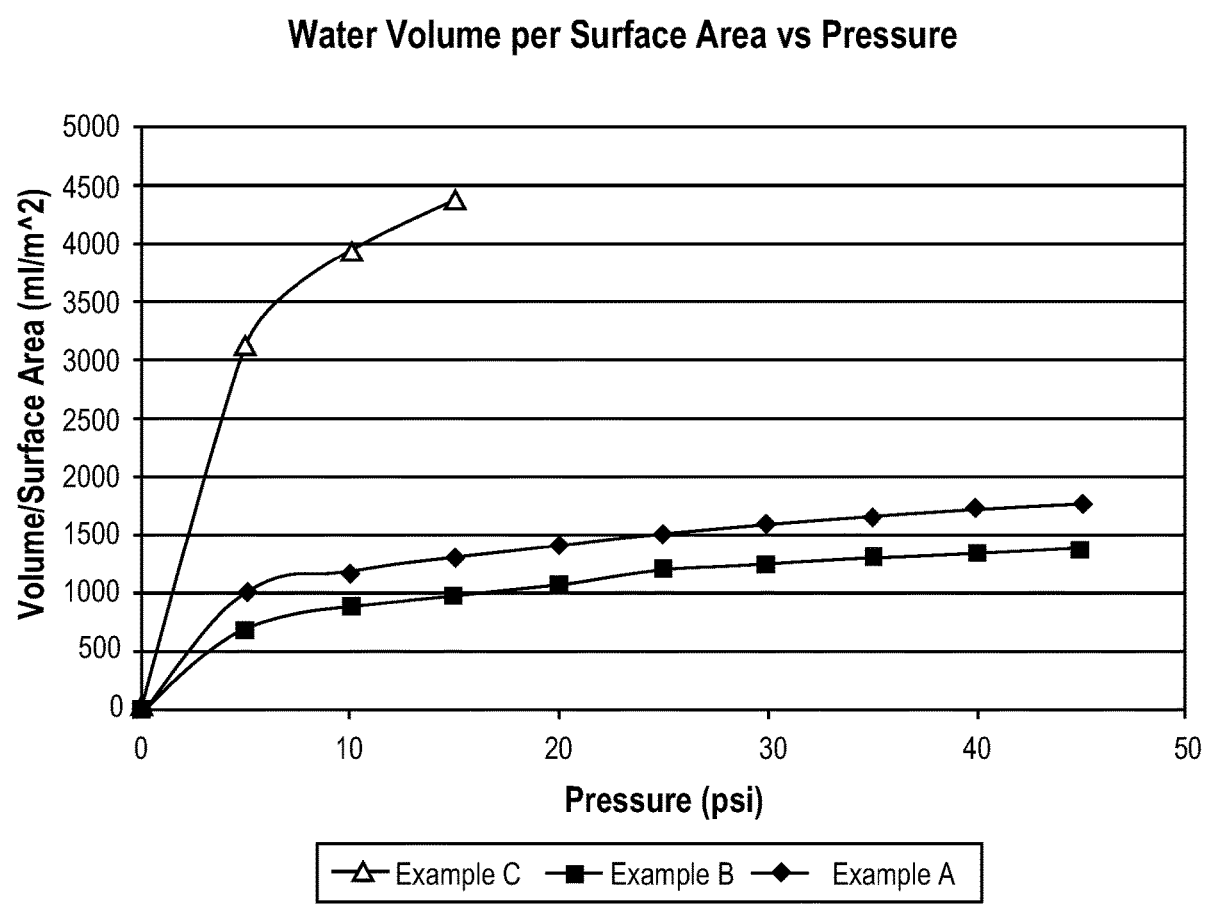
FIG. 14 is a graph illustrating water volume per surface area (Volume/Area) versus pressure for the two exemplary wraps of FIG. 12.

The results shown in FIG. 14 illustrate that a large fluid volume (Example C) is not functional at even moderate pressures, namely, above about 15 psi. Example C generally exhibited inferior performance at low pressure as well. For example, the bladder took longer to fill and circulate than desirable for typical operating settings. In large part because of the pressure limitations, the pump pressure and flow rate could not be increased to compensate for the larger volume either.

Between Example A and Example B, Example A—the reinforced bladder—was found to perform as well as Example B but experienced kinking less often across a wide pressure range. The wrap of Example B experienced occasional problems with kinking, whether partial or complete blocking of the fluid pathway. By contrast, the wrap of Example A experienced significantly less occurrences of kinking without deteriorating other performance factors.

What is claimed is:

1. A therapy wrap for providing treatment to an anatomical body part, the therapy wrap comprising:
    a flexible fluid bladder;
    a gas pressure bladder overlaying the flexible fluid bladder for applying a compressive force to the anatomical body part; and
    a reinforcement member disposed within the gas pressure bladder at one or more kink prone regions, the reinforcement member formed of a gas permeable material and has a donut shape
    wherein the reinforcement member is secured between opposing layers of the gas pressure bladder by a weld that passes through a central hole of the donut shape of the reinforcement member.

2. The therapy wrap of claim 1, wherein the reinforcement member is made from a porous material.

3. The therapy wrap of claim 2, wherein the porous material has an open cell foam structure that is gas permeable,
    wherein the reinforcement member is secured between opposing layers of the gas pressure bladder by a plurality of spot welds that pass through the central hole of the donut shape of the reinforcement member.

4. The therapy wrap of claim 1 further comprising:
    a second reinforcement member disposed within the gas pressure bladder at one or more kink prone regions, where the second reinforcement member is curvilinear.

5. The therapy wrap of claim 4, wherein the second reinforcement member is circular or oval shaped.

6. The therapy wrap of claim 4, wherein the size and shape of the reinforcement member is defined at least in part by a perimeter of the gas pressure bladder.

7. The therapy wrap of claim 4, wherein the size and shape of the reinforcement member is defined at least in part by one or more interior attachment features disposed within the gas pressure bladder.

8. The therapy wrap of claim 1 further comprising:
    a second reinforcement member disposed within the gas pressure bladder at one or more kink prone regions, where the second reinforcement member is rectilinear.

9. The therapy wrap of claim 8, wherein the second reinforcement member is square or rectangular.

10. The therapy wrap of claim 1, wherein the reinforcement member is provided on a substrate having a width corresponding to a width of the gas pressure bladder.

11. The therapy wrap of claim 1, wherein the reinforcement member is made from a material having a higher hardness (durometer) than a material of the gas pressure bladder.

12. The therapy wrap of claim 1, wherein the reinforcement member has variable bending strength along its length.

13. The therapy wrap of claim 1, wherein the reinforcement member is made from an adhesive.

14. The therapy wrap of claim 1, wherein the reinforcement member is made from an insulating material.

15. The therapy wrap of claim 1, wherein the reinforcement member is made from a batten, where the batten is flexible in one direction of bending and rigid in another direction of bending.

16. The therapy wrap of claim 1 further comprising:
    a second reinforcement member disposed within the gas pressure bladder at one or more kink prone regions, where the second reinforcement member has an elongated shape aligned with a direction of flow of a gas within the gas pressure bladder.

17. The therapy wrap of claim 1, wherein the reinforcement member includes a plurality of reinforcement members provided along an elongated line aligned with a direction of flow of a gas within the gas pressure bladder.

18. The therapy wrap of claim 1, wherein the reinforcement member is secured to the gas pressure bladder by one or more welds.

19. The therapy wrap of claim 1, wherein the reinforcement member is secured to the gas pressure bladder by an adhesive.

20. The therapy wrap of claim 1, wherein the reinforcement member has a thickness greater than a thickness of a wall of the gas pressure bladder.

\* \* \* \* \*